(12) United States Patent
Neschadim

(10) Patent No.: US 10,780,179 B2
(45) Date of Patent: Sep. 22, 2020

(54) CONJUGATES FOR THE TREATMENT OF CANCER TARGETED AT INTRACELLULAR TUMOR-ASSOCIATED ANTIGENS

(71) Applicant: IMMUNOBIOCHEM CORPORATION, Toronto (CA)

(72) Inventor: Anton Neschadim, Toronto (CA)

(73) Assignee: IMMUNOBIOCHEM CORPORATION, Toronto (CA)

(*) Notice: Subject to any disclaimer, the term of this patent is extended or adjusted under 35 U.S.C. 154(b) by 28 days.

(21) Appl. No.: 15/558,906

(22) PCT Filed: Mar. 18, 2016

(86) PCT No.: PCT/CA2016/050307
§ 371 (c)(1),
(2) Date: Sep. 15, 2017

(87) PCT Pub. No.: WO2016/145536
PCT Pub. Date: Sep. 22, 2016

(65) Prior Publication Data
US 2018/0078654 A1   Mar. 22, 2018

Related U.S. Application Data

(60) Provisional application No. 62/134,634, filed on Mar. 18, 2015.

(51) Int. Cl.
| | |
|---|---|
| A61K 39/00 | (2006.01) |
| C07K 16/30 | (2006.01) |
| A61K 47/68 | (2017.01) |
| C07K 16/40 | (2006.01) |
| G01N 33/574 | (2006.01) |
| C07K 16/28 | (2006.01) |

(52) U.S. Cl.
CPC ...... *A61K 47/6803* (2017.08); *A61K 47/6849* (2017.08); *A61K 47/6851* (2017.08); *A61K 47/6871* (2017.08); *C07K 16/2863* (2013.01); *C07K 16/30* (2013.01); *C07K 16/40* (2013.01); *C12Y 304/23005* (2013.01); *G01N 33/57496* (2013.01); *A61K 2039/812* (2018.08); *A61K 2039/884* (2018.08); *C07K 2317/21* (2013.01); *C07K 2317/24* (2013.01); *C07K 2317/54* (2013.01); *C07K 2317/55* (2013.01); *C07K 2317/569* (2013.01); *C07K 2317/622* (2013.01); *C07K 2317/73* (2013.01); *C07K 2317/77* (2013.01); *G01N 2333/96472* (2013.01)

(58) Field of Classification Search
CPC combination set(s) only.
See application file for complete search history.

(56) References Cited

U.S. PATENT DOCUMENTS

| | | | |
|---|---|---|---|
| 2014/0227175 A1 | 8/2014 | Vasiljeva et al. | |
| 2014/0308201 A1* | 10/2014 | Batt | A61K 31/5025 |
| | | | 424/1.49 |
| 2014/0322247 A1* | 10/2014 | Barsanti | C07D 233/64 |
| | | | 424/178.1 |

FOREIGN PATENT DOCUMENTS

| | | |
|---|---|---|
| WO | 00/55628 | 9/2000 |
| WO | 2012/175223 A1 | 12/2012 |

OTHER PUBLICATIONS

Bouchard et al (Biorganic and Medicinal Chemistry Letter, 24: 5357-65, 2014 (Year: 2014).*
Streckfus et al (Cancer Invest 18:101-109, 2000) (Year: 2000).*
Nakase et al Adv Drug Deliv Re 60:598-607, 2008 (Year: 2008).*
Khalkhali-Ellis et al (Plos one 9:e103230, Jul. 2014) (Year: 2014).*
Fauteaux et al., "Computational Selection of Antibody-drug Conjugate Targets for Brest Cancer", Oncotarget, vol. 7, No. 3, 2015, pp. 2555-2571.
The Human Protein Atlas, "The human secretome and membrane proteome", retrieved from: https://www.preoteinatlas.org/humanproteome/tissue/secretome, p. 1/5.
Zaidi et al., "Cathepsin D: A cellular roadmap", Biochemical and Biophysical Research Communications, 2008, 376, pp. 5-9.
Barok, Mark et al. Trastuzumab emtansine: mechanisms of action and drug resistance. Breast Cancer Research. Mar. 2014, 16(2):209.
Bouchard, Hervé et al. Antibody-drug conjugates—A new wave of cancer drugs. Bioorganic & Medicinal Chemistry~Letters 24(2014) 5357-5363.
Laurent-Marha, Valerie et al. Endocytosis of pro-cathepsin D into breast cancer cells is mostly independent of mannose-6-phosphate receptors. Journal of Cell Science 111, 2539-2549, 1998.
Garcia, Marcel et al. Characterization of Monoclonal Antibodies to the Estrogen-regulated Mr 52,000 Glycoprotein and Their Use in MCF7 Cells. Cancer Research, 45, 709-716, Feb. 1985.

(Continued)

*Primary Examiner* — Lei Yao
(74) *Attorney, Agent, or Firm* — Bereskin & Parr LLP; Carmela De Luca

(57) ABSTRACT

The present disclosure relates to conjugates, preferably, antibody-drug conjugates, directed against select non-transmembrane tumor antigens that are normally intracellular but can be secreted from cancer cells, such as human cathepsin D, and can be targeted in a way that enables the selective delivery of the conjugate to cancer cells. The design and mechanism of action disclosed enable the preferential delivery of the conjugate prodrug to cancer cells over normal cells for the purpose of selectively killing cancer cells. The uses of such conjugates for the treatment of cancer are described.

12 Claims, 10 Drawing Sheets

(56) References Cited

OTHER PUBLICATIONS

Abbott, Daniel E. et al. Reevaluating cathepsin D as a biomarker for breast cancer serum activity levels versus histopathology. Cancer Biol Ther. Jan. 2010 ; 9(1): 23-30.
Beaujouin, Mélanie et al. Pro-cathepsin D interacts with the extracellular domain of the B chain of LRP1 and promotes LRP1-dependent fibroblast outgrowth. Journal of Cell Science 123(19), 3336-3346, May 24, 2010.
Benes, Petr et al. Cathepsin D—Many functions of one aspartic protease. Crit Rev Oncol Hematol. Oct. 2008 ; 68(1): 12-28.
Capony, F. et al. Increased Secretion, Altered Processing, and Glycosylation of Pro-Cathepsin D in Human Mammary Cancer Cells. Cancer Res 1989;49:3904-3909.
Capony, Francoise et al. Specific Mannose-6-Phosphate Receptor-Independent Sorting of Pro-Cathepsin D in Breast Cancer Cells. Experimental Cell Research 215, 154-163 (1994).
Chai, Yun et al. The potential prognostic value of cathepsin D protein in serous ovarian cancer. Arch Gynecol Obstet(2012) 286:465-471.
Chambon, M. et al. Cathepsin D Cytosolic Assay and Immunohistochemical Quantification in Human Prostate Tumors. The Prostate 24:320-325 (1994).
Chari, Ravi V. J. Targeted Cancer Therapy: Conferring Specificity to Cytotoxic Drugs. Counts of Chemical Research 98-107 Jan. 2008 vol. 41, No. 1.
Derocq, D. et al. Cathepsin D is partly endocytosed by the LRP1 receptor and inhibits LRP1-regulated intramembrane proteolysis. Oncogene (2012) 31, 3202-3212.
Dian, D. et al., Expression of Cathepsin-D in Primary Breast Cancer and Corresponding Local Recurrence or Metastasis: An Immunohistochemical Study. Anticancer Research 32: 901-906 (2012).
El Melegy, N. T. et al. Potential biomarkers for differentiation of benign prostatic hyperplasia and prostate cancer. British Journal of Biomedical Science, 2010, 67 (3), 109-112.
Fukuda, mieko E. et al. Cathepsin D Is a Potential Serum Marker for Poor Prognosis in Glioma Patients. Cancer Res 2005; 65: (12). Jun. 15, 2005, 5190-5194.
Gandour-Edwards, Regina et al. Predictive Value of Cathepsin-D for Cervical Lymph Node Metastasis in Head and Neck Squamous Cell Carcinoma. Head & Neck Dec. 1999, 718-722.
Herz, Joachim et al. LRP: a multifunctional scavenger and signaling receptor. J. Clin. Invest. 108:779-784 (2001).
Hinrichs, Christian S. et al. Reassessing target antigens for adoptive T cell therapy. Nat Biotechnol. Nov. 2013; 31(11): 999-1008.
Huang, Liang et al. A Prognostic Model for Triple-Negative Breast Cancer Patients Based on Node Status, Cathepsin-D and Ki-67 Index. Dec. 2013. vol. 8, Issue 12, e83081, 1-7.
Khalkhali-Ellis, Zhila et al. Two Faces of Cathepsin D: Physiological Guardian Angel and Pathological Demon. Biol Med (Aligarh). ; 6(2), 1-17. 2014.
Kokkonen, Nina et al. Defective Acidification of Intracellular Organelles Results in Aberrant Secretion of Cathepsin D in Cancer Cells. The Journal of Biological Chemistry. vol. 279, No. 38, Issue of Sep. 17, pp. 39982-39988, 2004.
Laurent-Matha, Valérie et al. Procathepsin D Interacts with Prosaposin in Cancer Cells but its Internalization is not Mediated by LDL Receptor-Related Protein. Experimental Cell Research 277, 210-219 (2002).
Mbeunkui, Flaubert et al. Identification of Differentially Secreted Biomarkers using LC-MS/MS in Isogenic Cell Lines Representing a Progression of Breast Cancer. J Proteome Res. Aug. 2007 ; 6(8): 2993-3002.
Merseburger, Axel S. et al. Cathepsin DExpression in Renal Cell Cancer-Clinical Implications. European Urology 48 (2005) 519-526.
Miyake, Hideaki et al. Prediction of the extent of prostate cancer by the combined use of systematic biopsy and serum level of cathepsin D. International Journal of Urology (2003) 10, 196-200.
Nicotra, Giuseppina et al. The dilemma: Does tissue expression of cathepsin D reflect tumor malignancy? The question: Does the assay truly mirror cathepsin D misfunction in the tumor? Cancer Biomarkers 7 (2010) 47-64.
Nomura, Toshiyuki et al. Involvement of cathepsins in the invasion, metastasis and proliferation of cancer cells. The Journal of Medical Investigation, vol. 52, pp. 1-9 (2005).
Park, Hyung-Doo et al. Serum CA19-9, cathepsin D, and matrix metalloproteinase-7 as a diagnostic panel for pancreatic ductal adenocarcinoma. Proteomics 2012, 12, 3590-3597.
Perez, Edith A. Cardiac Toxicity of ErbB2-Targeted Therapies: What Do We Know? Clinical Breast Cancer, vol. 8, Suppl. 3, S114-S120, 2008.
Qi, Yi-Jun et al. Proteomic profiling of N-linked glycoproteins identifies ConA-binding procathepsin D as a novel serum biomarker for hepatocellular carcinoma. Proteomics 2014, 14, 186-195.
Ross, Jeffrey S. et al. Quantitative Immunohistochemical Determination of Cathepsin D Levels in Prostatic Carcinoma Biopsies. Anatomic Pathology, vol. 104(1), pp. 37-41, Jul. 1995.
Salama, Ragaa H. M. et al. Urinary Tumor Markers Could Predict Survival in Bladder Carcinoma. Ind J Clin Biochem (Jul.-Sep. 2013) 28(3):265-271.
Senter, Peter D. Potent antibody drug conjugates for cancer therapy. Current Opinion in Chemical Biology 2009, 13:235-244.
Trail, Pamela A. Antibody Drug Conjugates as Cancer Therapeutics. Antibodies 2013, 2, 113-129.
Tuminello, F. M. et al. Cathepsin D, B and L Circulating Levels as Prognostic Markers of Malignant Progression. Anticancer Research 16: 2315-2320 (1996).
Vashishta, Aruna et al. Pleiotropic Effects of Cathepsin D. Endocrine, Metabolic & Immune Disorders—Drug Targets, 2009, 9, 385-391.
Vetvicka, Vaclav et al. Procathepsin D in breast cancer: What do we know? Effects of ribozymes and other inhibitors. Cancer Gene Therapy (2002) 9, 854-863.
Wozniak, B. et al. The effect of combined therapy on activity of cathepsin D and alpha-1-antitrypsin in the blood serum of women with cervical cancer. Eur J. Gynaec. Oncol.—ISSN: 0392-2936XXIX, n. 6, 2008, pp. 617-620.
PCT/CA2016/050307 International Search Report and Written Opinion of the International Searching Authority, dated Jun. 23, 2016.
Thorpe P. E. et al., "The preparation and cytotoxic properties of antibody-toxin conjugates", Immunological Reviews, Wiley-Blackwell Publishing Inc, vol. 62, Jan. 1, 1982, pp. 119-158.

* cited by examiner

SMCC-DM1

(III)

SPDB-DM4

(IV)

SMCC-DM1 + Binding protein

(V)

SPDB-DM4 + Binding protein

(VI)

CONJUGATES FOR THE TREATMENT OF CANCER TARGETED AT INTRACELLULAR TUMOR-ASSOCIATED ANTIGENS

RELATED APPLICATIONS

This application is a national phase entry of PCT/CA2016/050307, filed Mar. 18, 2016, which claims priority from U.S. Provisional patent application Ser. No. 62/134,634 filed Mar. 18, 2015, each of these applications being incorporated herein in their entirety by reference.

FIELD OF THE INVENTION

The present disclosure relates to conjugates, preferably, antibody-drug conjugates, directed against select non-transmembrane tumor antigens that are normally intracellular and can be secreted from cancer cells, such as human cathepsin D or cathepsin E.

BACKGROUND

One of the challenges in treating cancer with targeted therapies is the selective recognition and killing of cancerous, malignant cells, while avoiding the infliction of damage on normal, non-transformed cells.

Research has identified a number of tumor-specific antigens (TSA) or tumor-associated antigens (TAA). A number of targeted biological therapeutics typically directed against one or more tumor-specific or tumor-associated antigens have been developed. These include monoclonal antibody therapeutics and, more, recently, potentiated antibody therapeutics, or antibody-drug conjugates (ADCs), which are biological prodrugs consisting of an antigen recognition moiety, a stable or cleavable linker, and a linker-attached drug (typically, a highly cytotoxic molecule). Antibody-drug conjugates may achieve specific killing of cancer cells because of the high activity of the cytotoxic payload they carry, the major obstacle being selectivity.

Tumor-specific or tumor-associated antigens typically include products of mutated proto-oncogenes, oncogenes, tumor suppressor genes, oncofetal antigens, altered cell surface proteins, cell type-specific differentiation antigens, and antigens produced by oncogenic viruses, or proteins whose normal pattern or level of expression has been altered in cancer. Tumor-specific or tumor-associated antigens identified and validated to date include CA-125, carcinoembryonic antigen (CEA), MUC-1, alphafetoprotein (AFP), melanoma-associate antigen (MAGE), CA-125 or MUC-16, and many others (Hinrichs and Restifo 2013). Tumor antigens with abnormal patterns or levels of expression in cancel cells compared to normal cells also include many cell surface-expressed proteins, including the transmembrane receptor proteins, such as EGFR and ERBB2 (HER2), that are often found overexpressed in cancer cells.

Many tumor-specific or tumor-associated target antigens have very heterogeneous patterns of expression in cancer and, once targeted, can lead to the development of resistance through negative selection and amplification of marker-negative cells. Target antigens that have a homogeneous expression profile within the tumor may be helpful.

A number of clinically-successful biological therapeutics have been developed that have a degree of selectivity for cancer cells versus normal based on the overexpression of select cell surface antigens, such as trastuzumab and its antibody-drug conjugate, trastuzumab emtansine, that target cancer cells overexpressing the HER2 antigen on their surface. High selectivity is important for a successful antibody-drug conjugate, since overall efficacy, or the therapeutic window of the antibody-drug conjugate, is defined by the careful balancing of activity against cancer with the safety and toxicity against normal cells.

Antibody therapeutics conventionally recognize and bind accessible, cell surface-exposed antigens, and practically all biological therapeutics in development or those approved in the clinic are targeted to cancer cells based on some cell surface-expressed antigen. This limitation extends to the existing members of the antibody-drug conjugate class of potentiated biologics, for which it is widely recognized that, with respect to target antigen selection, several criteria need to be fulfilled for therapeutic efficacy, including: (a) the antibody-drug conjugate has to be selective and recognize a cell surface-expressed tumor antigen (that is selectively expressed on or overexpressed on cancer cells vs. normal); and, (b) the target antigen of the antibody-drug conjugate has to be able to facilitate its internalization into the cell for the release of the cytotoxic payload (Chari 2008; Trail 2013). For example, trastuzumab emtansine, that as mentioned is an antibody-drug conjugate recognizing an ectopic antigen on the HER2 receptor, derives selectivity from the overexpression of the HER2 receptor on certain cancers, and activity from the high rate of internalization of this receptor: antibody-drug conjugate complex and degradation in the lysosomes—the latter resulting in the release of the toxic payload (Barok, Joensuu et al. 2014). It is also known that because of the expression of tumor antigens on normal cells, antibody-drug conjugates can produce significant on-target toxicities directed against non-cancerous cells expressing substantial levels of their target receptors that result in conjugate internalization (Perez 2008; Bouchard, Viskov et al. 2014). This may limit the antibody-drug conjugate use against a particular antigen. It is estimated that more than 100 different antibody-drug conjugates targeted at some cell-surface expressed, transmembrane tumor antigen are currently at various stages of preclinical and clinical development.

However, the majority of useful tumor antigens, or cancer biomarkers, that are only expressed or are abnormally expressed in cancer cells are intracellular proteins. Subsequently, their presence cannot be easily detected and/or recognized on the surface of the cells. Such tumor antigens or cancer biomarkers are currently considered undruggable to conventional biological therapeutics, including antibody-drug conjugates. Examples include such antigens as BCR-ABL, BRCA1/2, BRAF V600E, 5100 proteins, KRAS, MYC family of proteins and p53. The targeted therapies currently available against tumors identified by the abnormal expression or activity of such biomarkers are typically small molecule-based. For example, BCR-ABL is an oncogenic product that results from an aberrant chromosomal translocation. Tumors in which BRC-ABL drivers oncogenic growth can be targeted with the tyrosine kinase inhibitor, imatinib, which is a small-molecule with high specificity for this mutant protein.

The current criteria for ADC design include that internalizing antibody-drug conjugates be directed at a cell surface-expressed receptor to achieve sufficient internalization for the antibody-drug conjugate to be therapeutically effective (Chari 2008; Senter 2009; Trail 2013) and that antibody-drug conjugates be actively internalized, i.e., internalized by receptor-mediated endocytosis, to achieve sufficient accumulation in targeted cells and therapeutic activity (Chari 2008; Senter 2009; Trail 2013). There have been many recent advances in antibody-drug conjugate technologies, including improvements to the toxic payloads, improvements to conjugation methods and their specificity, improvements to the linker design and activation mechanisms, development of Probody™-drug conjugates (Probodies are proteolytically activated antibodies engineered to remain inert until activated locally in diseased tissue), and identification of novel surface markers that are suitable targets for this technology. The current focus of emerging technologies is mainly on broadening the therapeutic window of the antibody-drug conjugates, with the secondary focus being on identifying new cell surface-expressed tumor antigens as suitable and selective targets.

US Patent application US2014/0227175 describes cysteine protease Cathepsin-binding compounds bound to a carrier comprising a therapeutic and/or diagnostic moiety, for use in the diagnosis and/or treatment of inflammatory diseases, and/or for use in the diagnosis and/or treatment of neoplastic diseases, where the Cathepsin-binding compounds are described to bind to inflammatory cells of the tumor stroma.

SUMMARY

In the current disclosure, it is demonstrated that antibody-drug conjugates that specifically bind human aspartic protease cathepsin D and/or pro-cathepsin D, neither of which are transmembrane receptors, can be used to target and kill cancer cells. Without wishing to be bound by theory, select normally intracellular protein targets that are secreted from disease cells and are taken back up by the cells (reinternalized, or recaptured) for example by receptor-mediated endocytosis, passive endocytosis, or pinocytosis may be used to cytotoxically target the disease cell.

In the current disclosure, it is also demonstrated that such antibody-drug conjugates directed at extracellular human cathepsin D and its isoforms, can be used to selectively target and kill cancer over normal cells (see for example FIGS. 3, 4 and 8). Further as shown in Table 2, anti-cathepsin D ADCs have a comparable IC50 to anti-EGFR ADCs on breast cancer cell lines. The anti-cathepsin D ADCs IMB-101 and IMB-102, are however shown to be less toxic to normal cells than either EGFR ADCs IMB-701 or IMB-702.

Without wishing to be bound by theory, it is believed that the selective targeting may result since the cancer cells and not normal cells primarily secrete or hypersecrete the particular target antigen and re-internalize it. Such antibody-drug conjugates may be efficacious and selective whether the protein target is re-internalized by cancer cells only or by both cancer cells and normal cells. The selectivity, it is believed, is primarily conferred by the lack of target protein secretion by normal cells, in which it retains its intracellular localization, and the secretion of the protein target by cancer cells, a large fraction of which may remain in the extracellular environment and immediate vicinity of the tumor, and a fraction of which is re-internalized by cancer cells. Additional selectivity is conferred for some target antigens by the presence or amplification of specific receptor-mediated endocytosis mechanisms for target re-internalization on tumor cells and tumor-associated stroma, such as cancer-associated fibroblasts, but the lack or under-expression of such a receptor or mechanism for target re-internalization on normal cells.

Bystander tumor cell killing may also result from antibody-drug conjugate internalization. For example, a target antigen secreted by some of the cells in a tumor could be complexed with the antibody-drug conjugate and be then internalized by other cells that can internalize the target antigen. This includes bystander effects due to the internalization of the target antigen-antibody-drug conjugate complex by cancer-associated fibroblasts, which support tumor growth.

Accordingly, in one aspect the disclosure provides a conjugate comprising:
 a. a targeting agent that specifically binds human cathepsin D target antigen;
 b. a cytotoxic moiety, optionally linked directly or indirectly to the targeting agent; and
 c. optionally, a linker linking the targeting agent and cytotoxic moiety.

In an embodiment, the conjugate is an antibody-drug conjugate that has one or more of the following features: (a) selective for cancer cells compared to normal cells; (b) capable of recognizing or targeting cancer cells based on an abnormal or irregular pattern of expression of a tumor antigen or cancer biomarker that is a non-transmembrane protein, is not cell surface expressed and/or normally has an intracellular pattern of expression; and, (c) is cytotoxic to tumor cells based on the targeting via the said tumor antigen or cancer biomarker.

In an embodiment, the antibody drug conjugate specifically binds to human cathepsin D or pro-cathepsin D, which are cancer biomarkers and/or tumor antigens that are normally intercellular but can be abnormally secreted from cancer cells.

The present disclosure describes in an embodiment, antibody-drug conjugates comprising potent cytotoxic payloads or toxins ("cytotoxic moieties"). In an embodiment, the ADC includes a toxin with an IC50 concentration (as assessed against a number of cancer cell lines with free toxin) of pM to low nM range (Trail 2013).

Further it is demonstrated herein that the cathepsin D ADCs show selective killing against different cancer types (FIGS. 3, 4 and 8).

Accordingly, in an embodiment this disclosure provides a method of delivering a cytotoxin selectively to cancer cells, the method comprising contacting the cancer cells with the conjugate described herein or with a composition comprising such conjugate.

In another aspect, this disclosure provides a method of selecting an intracellular tumor antigen as a target for the generation of a selective targeting agent-drug conjugate such as an antibody-drug conjugate, the method comprising:
 (i) testing non-cancer cells for a candidate antigen to determine if it is intracellular and/or normally non-secreted by non-cancer cells;
 (ii) testing cancer cells for the candidate antigen to determine if it is secreted by cancer cells;
 (iii) if the target antigen is secreted by cancer cells in an amount greater than the non-cancer cells, testing cancer cells for the candidate antigen to determine if it can be re-internalized by cancer cells.
 (iv) identifying a target antigen that is secreted by cancer cells in an amount greater than non-cancer cells and is reinternalizable by cancer cells as a candidate target intracellular tumor antigen.

Described herein in an embodiment, are antibody-drug conjugates directed at non-transmembrane, normally intracellular tumor antigens. Antibody-drug conjugates directed at the human cathepsin D tumor antigens that are selective and active against cancer cells are described. The antibody-drug conjugates may also offer minimal or no toxicity against normal cells.

Antibodies for cathepsins, including human cathepsin and pro-cathepsin D are known in the art. Antibodies that bind and/or are specific for natively-folded cathepsin D can be used to produce the antibody-drug conjugates specific for cathepsin D described herein.

Cathepsin D is a lysosomal aspartyl protease involved in protein degradation and tissue remodeling. The expression of human cathepsin D or its known isoforms, such as pro-cathepsin D, in cancer cells or its abnormal secretion from cancer cells has been associated with the presence of cancer, more aggressive cancer growth and progression, metastasis, and/or cancer prognosis (Nomura and Katunuma 2005; Wozniak, Mila-Kierzenkowska et al. 2008; Vashishta, Ohri et al. 2009; Abbott, Margaryan et al. 2010; Dian, Vrekoussis et al. 2012; Vetvicka and Fusek 2012; Khalkhali-Ellis and Hendrix 2014). Specifically, cathepsin D and/or pro-cathepsin D have been suggested as useful biomarkers in multiple cancers, including: breast cancer, including triple-negative breast cancer, prostate cancer, ovarian cancer, endometrial cancer, non-small cell lung cancer (NSCLC), hepatocellular carcinoma (HCC), head & neck squamous cell carcinoma (HNSCC), bladder cancer, pancreatic cancer, glioblastoma multiforme (GBM), small-cell lung cancer, renal cell carcinoma, melanoma, and other cancers (Chambon et al, 1994; Makar et al, 1994; Ross et al, 1995, Nicotra et al, 2010; Sloman, D'Amico et al. 1996; Tumminello, Leto et al. 1996; Wang and Zhao 1998; Gandour-Edwards, Trock et al. 1999; Hara, Miyake et al. 2002; Lentari, Segas et al. 2002; Miyake, Hara et al. 2003; Fukuda, Iwadate et al. 2005; Merseburger, Hennenlotter et al. 2005; Nomura and Katunuma 2005; Mbeunkui, Metge et al. 2007; Vashishta, Ohri et al. 2009; El Melegy, Aboulella et al. 2010; Chai, Wu et al. 2012; Park, Kang et al. 2012; Huang, Liu et al. 2013; Salama, Selem et al. 2013; Qi, Ward et al. 2014). The preceding list is not meant to be exhaustive.

Human cathepsin D is secreted from cancer cells and was shown to be re-internalized by cancer cells by active endocytosis (Capony, Braulke et al. 1994; Laurent-Matha, Farnoud et al. 1998; Benes, Vetvicka et al. 2008). Mechanisms and receptors that have been implicated to play a role in the receptor-mediated internalization, include mannose-6-phosphate, LDL receptor-related protein (LRP or LRP1), and possibly others (Laurent-Matha, Farnoud et al. 1998; Herz and Strickland 2001; Laurent-Matha, Lucas et al. 2002; Beaujouin, Prebois et al. 2010; Derocq, Prebois et al. 2012).

Defective acidification of intracellular organelles in cancer cells has been suggested as one of the mechanisms resulting in the aberrant secretion of lysosomal proteins, such as the lysosomal hydrolase cathepsin D and its isoforms, that normally have intracellular localization and are not secreted (Kokkonen, Rivinoja et al. 2004).

Without wishing to be bound to theory, the herein disclosed antibody-drug conjugate may utilize a "Trojan horse" approach to gain access into the cell by hijacking human cathepsin D, abnormally secreted from cancer cells, for the purpose of entry. Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which.

Figure 1:
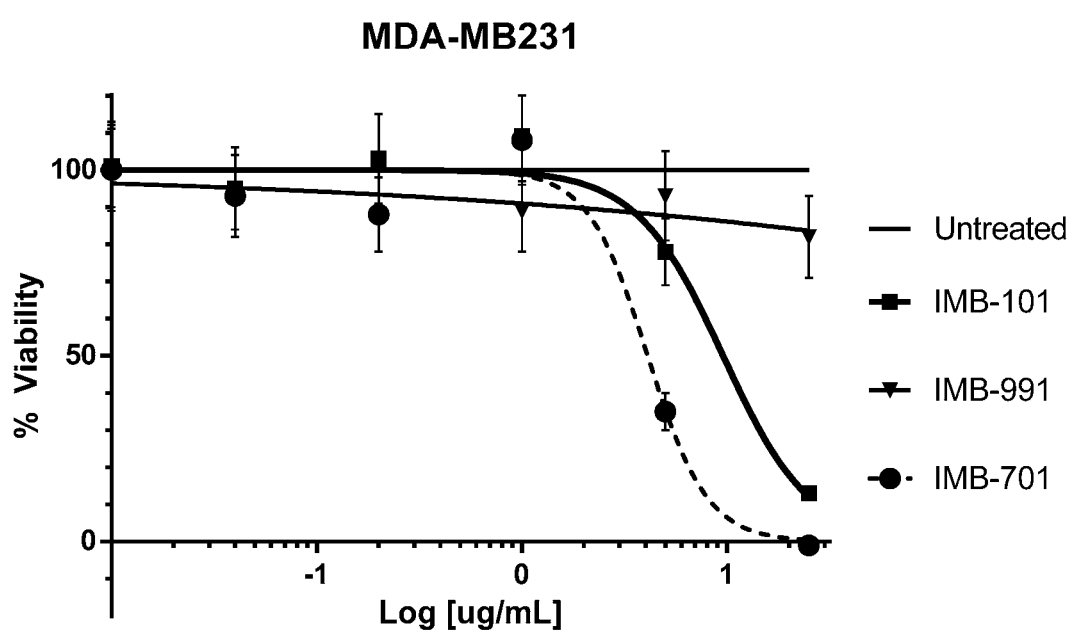
FIG. 1 is a graph depicting the measurement of the cytotoxic activity of the SMCC-DM1 antibody-drug conjugates of anti-human cathepsin D, anti-human EGFR, and appropriate isotype controls, against the MDA-MB-231 breast cancer cell line by a colorimetric cell proliferation assay (MTS). IMB-101—anti-human cathepsin D-SMCC-DM1; IMB-102—anti-human cathepsin D-SPDB-DM4; IMB-701—anti-human EGFR-SMCC-DM1; IMB-702—anti-human EGFR-SPDB-DM4; IMB-991—isotype-matched monoclonal-SMCC-DM1; IMB-992—isotype-matched monoclonal-SPDB-DM4.
Figure 2:
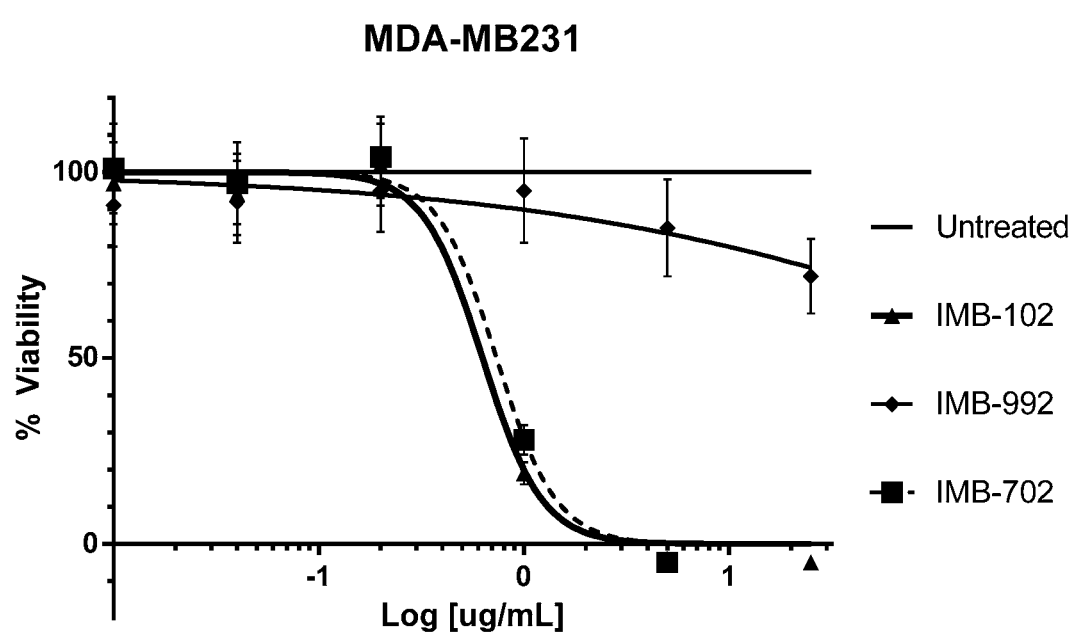
FIG. 2 is a graph depicting the measurement of the cytotoxic activity of the SPDB-DM4 antibody-drug conjugates of anti-human cathepsin D, anti-human EGFR, and appropriate isotype controls, against the MDA-MB-231 breast cancer cell line by a colorimetric cell proliferation assay (MTS). IMB-101—anti-human cathepsin D-SMCC-DM1; IMB-102—anti-human cathepsin D-SPDB-DM4; IMB-701—anti-human EGFR-SMCC-DM1; IMB-702—anti-human EGFR-SPDB-DM4; IMB-991—isotype-matched monoclonal-SMCC-DM1; IMB-992—isotype-matched monoclonal-SPDB-DM4.
Figure 3:
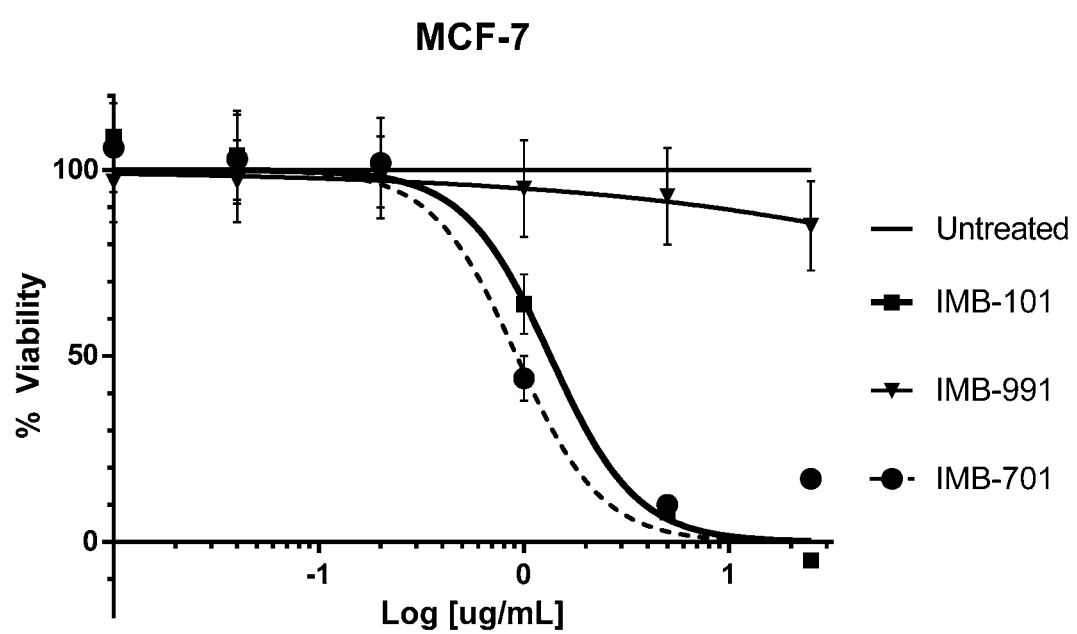
FIG. 3 is a graph depicting the measurement of the cytotoxic activity of the SMCC-DM1 antibody-drug conjugates of anti-human cathepsin D, anti-human EGFR, and appropriate isotype controls, against the MCF-7 breast cancer cell line by a colorimetric cell proliferation assay (MTS). IMB-101—anti-human cathepsin D-SMCC-DM1; IMB-102—anti-human cathepsin D-SPDB-DM4; IMB-701—anti-human EGFR-SMCC-DM1; IMB-702—anti-human EGFR-SPDB-DM4; IMB-991—isotype-matched monoclonal-SMCC-DM1; IMB-992—isotype-matched monoclonal-SPDB-DM4.
Figure 4:
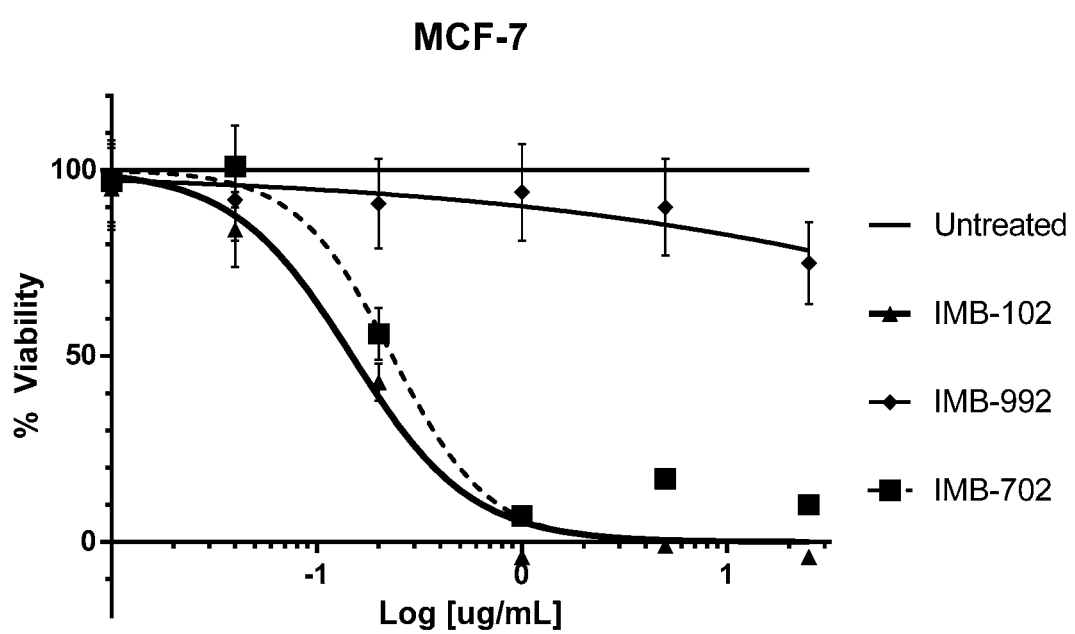
FIG. 4 is a graph depicting the measurement of the cytotoxic activity of the SPDB-DM4 antibody-drug conjugates of anti-human cathepsin D, anti-human EGFR, and appropriate isotype controls, against the MCF-7 breast cancer cell line by a colorimetric cell proliferation assay (MTS). IMB-101—anti-human cathepsin D-SMCC-DM1; IMB-102—anti-human cathepsin D-SPDB-DM4; IMB-701—anti-human EGFR-SMCC-DM1; IMB-702—anti-human EGFR-SPDB-DM4; IMB-991—isotype-matched monoclonal-SMCC-DM1; IMB-992—isotype-matched monoclonal-SPDB-DM4.
Figure 5:
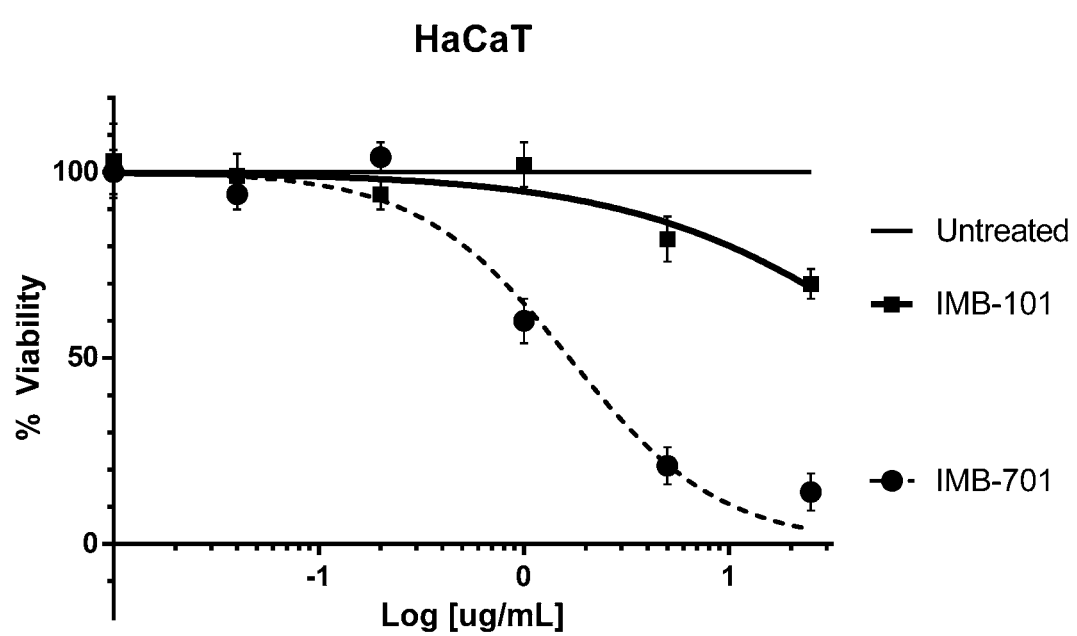
FIG. 5 is a graph depicting the measurement of the cytotoxic activity of the SMCC-DM1 antibody-drug conjugates of anti-human cathepsin D and anti-human EGFR, against the normal, immortalized human keratinocyte cell lines, HaCaT, by a colorimetric cell proliferation assay (MTS). IMB-101—anti-human cathepsin D-SMCC-DM1; IMB-102—anti-human cathepsin D-SPDB-DM4; IMB-701—anti-human EGFR-SMCC-DM1; IMB-702—anti-human EGFR-SPDB-DM4; IMB-991—isotype-matched monoclonal-SMCC-DM1; IMB-992—isotype-matched monoclonal-SPDB-DM4.
Figure 6:
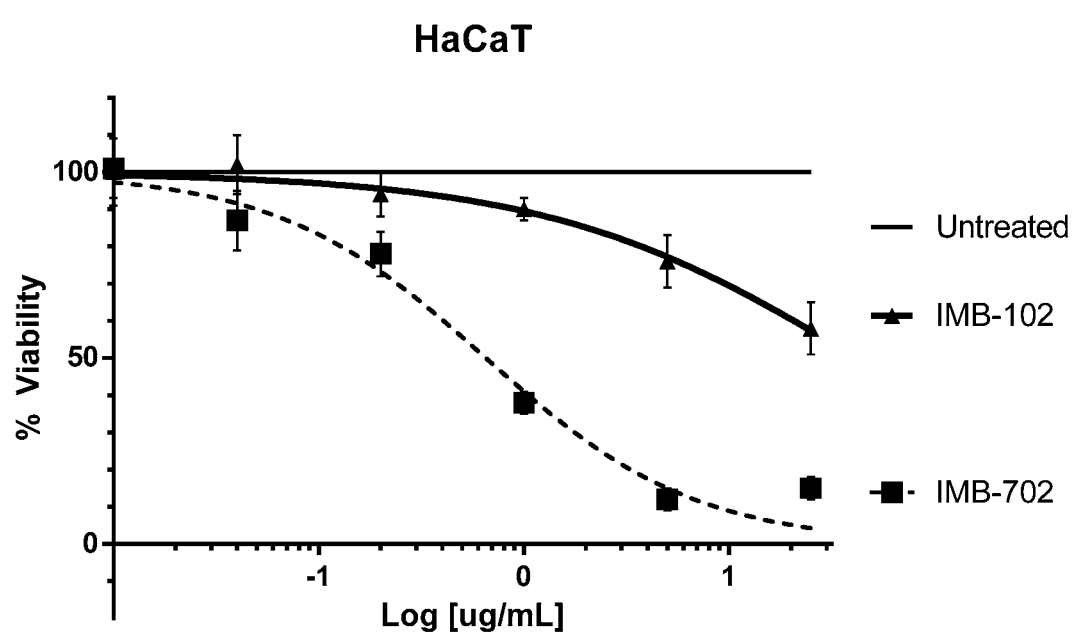
FIG. 6 is a graph depicting the measurement of the cytotoxic activity of the SPDB-DM4 antibody-drug conjugates of anti-human cathepsin D and anti-human EGFR, against the normal, immortalized human keratinocyte cell lines, HaCaT, by a colorimetric cell proliferation assay (MTS). IMB-101—anti-human cathepsin D-SMCC-DM1; IMB-102—anti-human cathepsin D-SPDB-DM4; IMB-701—anti-human EGFR-SMCC-DM1; IMB-702—anti-human EGFR-SPDB-DM4; IMB-991—isotype-matched monoclonal-SMCC-DM1; IMB-992—isotype-matched monoclonal-SPDB-DM4.

Table 1 is summarizes the antibody-drug conjugates synthesized and the characterization of their approximate payload (Drug:Antibody Ratio), as determined spectrophotometrically.

Table 2 summarizes the 50% inhibitory concentrations (IC50) calculated for the antibody-drug conjugates tested on the MCF-7, MDA-MB-231 and HaCaT cell lines. (Data corresponds to FIGS. 1-6).

DETAILED DESCRIPTION

I. Definitions

Unless stated otherwise, the following terms and phrases as used herein are intended to have the following meanings:

When trade names are used herein, applicants intend to independently include the trade name product formulation, the generic drug, and the active pharmaceutical ingredient(s) of the trade name product.

The term "human cathepsin D" as used herein refers to any protein that comprises the expressed (including pro-cathepsin D) and processed forms of the human (*Homo sapiens*) CTSD gene, also known as CPSD, CLN10, and HEL-S-130P, wherein the protein is designated as UniProtKB/Swiss-Prot P07339 (NCBI Reference Sequence: NP_001900.1, mature peptide corresponding to amino acid residues 65-412). The term "cathepsin D" as used herein may refer to the wild type protein and all naturally occurring variants thereof, including pro-cathepsin D (UniProtKB/Swiss-Prot P07339 and NCBI Reference Sequence: NP_001900.1, amino acid residues 19-412) and pre-pro-cathepsin D (UniProtKB/Swiss-Prot P07339 and NCBI Reference Sequence: NP_001900.1, amino acid residues 1-412), and all transcriptional variants, post-translationally-modified variants (known post-translational modifications of human cathepsin D are described as part of the record in UniProtKB/Swiss-Prot P07339), and processed forms of human cathepsin D, including, without limitation, cathepsin D light chain (UniProtKB/Swiss-Prot P07339 and NCBI Reference Sequence: NP_001900.1, amino acid residues 65-161), cathepsin D heavy chain (UniProtKB/Swiss-Prot P07339 and NCBI Reference Sequence: NP_001900.1, amino acid residues 169-412), and cathepsin D activation peptide (UniProtKB/Swiss-Prot P07339 and NCBI Reference Sequence: NP_001900.1, amino acid residues 19-64), whether catalytically active or not.

The term "cancer cell" as used herein refers to cells from or derived from a cancer, including a cancer cell line, and which are malignant, neoplastic, and/or capable of causing cancer, in a subject. For example, cells that are part of a tumor, cancer cells that can give rise to a tumor, and cells in a progressive malignant state are included.

The term "normal cell" as used herein refers to cells that are non-cancerous, non-malignant, and includes healthy cells (e.g. of the same type or lineage as cancer cells in methods where normal cells and cancer cells are being compared) and may include, for example, immortalized or immortal cells, if such cells are not expected to cause disease or cancer in a healthy subject.

The term "intracellular" as used herein refers to a protein that is found under normal conditions inside one of the sub-cellular compartments, for example, endocytic, nuclear or mitochondrial, or a non-compartmentalized protein present in the cytoplasm.

The term "target antigen" as used herein refers to a substance optionally a protein that is indicative of the presence of cancer in the body, and/or is preferentially expressed or overexpressed by cancer cells and secreted or specifically secreted by cancer cells. It includes but is not limited to tumor antigens.

The term "tumor antigen" as used herein refers to a substance optionally a protein that is produced by tumor cells and includes "tumor-associated antigen" or "TAA" which refers to a protein that is produced in tumor cells and is differentially expressed in a cancer compared to a corresponding normal tissue, as well as "tumor-specific antigen" or "TSA" which refers to a tumor antigen that is produced in tumor cells and is specifically or abnormally expressed in a cancer compared to a corresponding normal tissue.

The term "specifically secreted by cancer cells" as used herein means that the protein is secreted by a cancer cell compared to its non-cancer precursor by at least an increase in quantity of 25%, 50%, 75%, or 100%.

Antibodies to human cathepsin D, pro-cathepsin D, and all isoforms, are available commercially from a number of sources, including, for example, the MAB1014 clone #185111 from R&D Systems, Minneapolis, Minn., USA, and clone 3F12-1B9 from Abnova, Taipei, Taiwan. Other antibodies for cathepsin D, including pro-cathepsin D, and all isoforms, are available from Dr. Marcel Garcia (Institut des Biomolécules Max Mousseron (IBMM), France), including for example the M1G8 clone (Laurent-Matha et al. 1998; Garcia et al. 1985.)

The term "polypeptide" or "protein" as used herein refers to a molecule comprised of amino acid residues (e.g. naturally occurring residues, and/or non-naturally occurring residues), including for example single chain polypeptides, as well as a single chain of a multichain protein, multichain proteins such as traditional antibodies, recombinant polypeptides including for example fusion proteins, tagged proteins, mutant proteins and fragments, typically active fragments, of full length proteins. Protein and polypeptide are herein used interchangeably.

The term "polynucleotide" or "nucleic acid molecule" as used herein refers to a linked series of nucleoside or nucleotide monomers consisting of naturally occurring bases, sugars and intersugar (backbone) linkages, including for example cDNA, vectors and recombinant polynucleotides. The term also includes modified or substituted sequences comprising non-naturally occurring monomers or portions thereof, which function similarly. Such modified or substituted nucleic acid molecules may be preferred over naturally occurring forms because of properties such as enhanced cellular uptake, or increased stability in the presence of nucleases. The term also includes chimeric nucleic acid molecules that contain two or more chemically distinct regions. For example, chimeric nucleic acid molecules may contain at least one region of modified nucleotides that confer beneficial properties (e.g. increased nuclease resistance, increased uptake into cells), or two or more nucleic acid molecules described herein may be joined to form a chimeric nucleic acid molecule. The polynucleotides may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. Also, the term "nucleic acid" can be either double stranded or single stranded, and represents the sense or antisense strand. Further, the term "nucleic acid" includes the complementary nucleic acid sequences.

The term "targeting agent" as used herein means any binding protein including antibodies, affimers and receptors, any nucleic acid, such as DNA, RNA or an aptamer that specifically binds a target antigen.

The term "antibody" herein is used in the broadest sense and includes monoclonal antibodies, polyclonal antibodies, single chain antibodies, dimers, multimers, multispecific antibodies (e.g., bispecific antibodies), and antibody fragments of any thereof, so long as they exhibit the desired biological activity (Miller et al (2003) Jour. of Immunology 170:4854-4861) as well as chimeric antibodies, including for example humanized antibodies. Antibodies may be murine, human, humanized, chimeric, or derived from other species. Human antibodies can be isolated for example from a phage display library. An antibody includes a full-length immunoglobulin molecule or an immunologically active portion of a full-length immunoglobulin molecule, i.e., a molecule that contains an antigen binding site that immunospecifically binds an antigen of a target of interest or part thereof. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin. The antibody may be from recombinant sources and/or produced in transgenic animals.

"Antibody fragments" comprise a portion of a full length antibody, generally the antigen binding or variable region thereof. Examples of antibody fragments include Fab, Fab', F(ab')2, and Fv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques. Antibody fragments mean binding fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al (1975) Nature 256:495, or may be made by recombinant DNA methods (see, U.S. Pat. No. 4,816,567 herein incorporated by reference). The monoclonal antibodies may also be isolated from phage antibody libraries using the techniques described in Clackson et al (1991) Nature, 352:624-628; Marks et al (1991) J. Mol. Biol., 222:581-597; for example, both of which are incorporated herein by reference.

The antibodies herein specifically include "chimeric" antibodies, including humanized antibodies and chimeric monoclonal antibodies, in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855, each reference incorporated by reference). Chimeric antibodies of interest herein include "primatized" antibodies comprising variable domain antigen-binding sequences derived from a non-human primate (e.g., Old World Monkey or Ape) and human constant region sequences.

An "intact antibody" herein is one comprising a VL and VH domains, as well as a light chain constant domain (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include Clq binding; complement dependent cytotoxicity; Fc receptor binding; antibody-dependent cell-mediated cytotoxicity (ADCC); phagocytosis; and down regulation of cell surface receptors such as B cell receptor and BCR.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Single-chain Fv" or "scFv" mean single chain variable region antibody fragments which comprise the VH and VL domains of antibody, wherein these domains are present in a single polypeptide chain. The Fv polypeptide may further comprise a polypeptide linker between the VH and VL domains which enables the scFv to form the desired structure for antigen binding (Plückthun in The Pharmacology of Monoclonal Antibodies, vol. 113, Rosenburg and Moore eds., Springer-Verlag, New York, pp. 269-315 (1994). Anti-ErbB2 antibody scFv fragments are described in WO 93/16185; U.S. Pat. Nos. 5,571,894; 5,587,458.

The term "diabodies" refers to small antibody fragments with two antigen-binding sites, which fragments comprise a variable heavy domain (VH) connected to a variable light domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al (1993) Proc. Natl. Acad. Sci. USA 90:6444-6448.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al (1986) Nature, 321:522-525; Riechmann et al (1988) Nature 332:323-329; and Presta, (1992) Curr. Op. Struct. Biol., 2:593-596.

A targeting agent, such as an antibody "which specifically binds" a target antigen of interest, e.g., cathepsin D antigen, is one capable of binding that antigen with a KD $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Where the antibody is one which binds cathepsin D, it will usually preferentially bind cathepsin D as opposed to other cathepsin family members, for example at least 2×, 3×, 5× or more specifically, and may be one which does not significantly cross-react with other proteins. For example, in some embodiments, the extent of binding of the antibody to these other proteins (e.g., cell surface binding to endogenous receptor) will be less than 10% as determined by fluorescence activated cell sorting (FACS) analysis or radioimmunoprecipitation (RIA).

The terms "treat" or "treatment" refer to both therapeutic treatment and prophylactic or preventative measures, wherein the object is to prevent or slow down (lessen) an undesired physiological change or disorder, such as the development or spread of cancer. For purposes of this disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "therapeutically effective amount" refers to an amount of a conjugate effective to treat a disease or disorder in a mammal. In the case of cancer, the therapeutically effective amount of the conjugate may: (i) reduce the number of cancer cells; (ii) reduce the tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; and/or (vi) relieve to some extent one or more of the symptoms associated with the cancer. To the extent the conjugate may prevent growth and/or kill existing cancer cells, it may be cytostatic and/or cytotoxic. In animal models, efficacy may be assessed by physical measurements of the tumor during the course following administration of the conjugate, optionally ADC, and by determining partial and complete remission of tumor. For cancer therapy, efficacy can, for example, be measured by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, gastrointestinal stromal tumor (GIST), pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. Cancers that have been demonstrated to overexpress and/or secrete cathepsin D or procathepsin D, include but are not limited to breast cancer, triple-negative breast cancer, prostate cancer, ovarian cancer, non-small cell lung cancer (NSCLC), hepatocellular carcinoma (HCC), head & neck squamous cell carcinoma (HNSCC), bladder cancer, pancreatic cancer, glioblastoma multiforme (GBM), small-cell lung cancer, endometrial cancer, melanoma, and renal cell carcinoma.

A cancer which "overexpresses" a target antigen, e.g. cathepsin D, is one which has significantly higher levels of the protein, such as cathepsin D, compared to a noncancerous cell of the same tissue type. Such overexpression may be caused by gene amplification or by increased transcription or translation. Overexpression of a target antigen can be assessed prior to treatment. For example, cathepsin D overexpression may be determined in a diagnostic or prognostic assay by evaluating increased levels of the cathepsin D protein present inside cells or in the circulation (e.g., via an immunohistochemistry assay; IHC). Alternatively, or additionally, one may measure levels of cathepsin D-encoding nucleic acid in the cell, e.g., via fluorescent in situ hybridization (FISH; see WO 98/45479), southern blotting, or polymerase chain reaction (PCR) techniques, such as real time quantitative PCR(RT-PCR). One may also study cathepsin D overexpression by measuring shed antigen (e.g., cathepsin D or pro-cathepsin D) in a biological fluid such as serum (see, e.g., U.S. Pat. No. 4,933,294; WO 91/05264; U.S. Pat. No. 5,401,638). Aside from the above assays, various other in vivo assays are available to the skilled practitioner. For example, one may expose cells within the body of the patient to an antibody which is optionally labeled with a detectable label, e.g., a diagnostic radioactive isotope, and binding of the antibody to cells in the patient can be evaluated, e.g., by external scanning for radioactivity or by analyzing a biopsy taken from a patient.

The term "cytotoxic moiety" as used herein refers to a substance that causes destruction of cells. The term is intended to include radioactive isotopes (e.g., 211At, 131I, 125I, 90Y, 186Re, 188Re, 153Sm, 212Bi, 32P, 60C, and radioactive isotopes of Lu), chemotherapeutic agents, and toxins such as small molecule toxins or enzymatically active toxins of bacterial, fungal, plant or animal origin, including ricin, abrin, modeccin, viscumin, bacterial toxin proteins such as cholera, *E. coli.* heat-labile, pertussis, tetanus, botulinum, *pseudomonas, shigella*, and diphtheria toxins (this is list is not exhaustive), including synthetic analogs and derivatives thereof, including the maytansinoid, auristatin, calicheamicin, duocarmycin, PDB dimers, and alpha-amanitin drug moieties.

"Maytansinoid drug moiety" means the cytotoxic moiety of a targeting agent-drug conjugate that has the structure of a maytansine compound or a derivative or analogue thereof. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and maytansinol analogues have been reported. See U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, and Kawai et al (1984) Chem. Pharm. Bull. 3441-3451), each of which are expressly incorporated by reference.

A "chemotherapeutic agent" is a chemical compound useful in the treatment of cancer. Examples of chemotherapeutic agents include erlotinib (TARCEVA®, Genentech/OSI Pharm.), bortezomib (VELCADE®, Millenium Pharm.), fulvestrant (FASLODEX®, Astrazeneca), sunitinib (SUTENT®, SU11248, Pfizer), letrozole (FEMARA®, Novartis), imatinib mesylate (GLEEVEC®, Novartis), PTK787/ZK 222584 (Novartis), oxaliplatin (ELOXATIN®, Sanofi), 5-FU (5-fluorouracil), leucovorin, rapamycin (Sirolimus, RAPAMUNE®, Wyeth), lapatinib (TYKERB®, GSK572016, GlaxoSmithKline), lonafarnib (SARASAR®, SCH 66336), sorafenib (NEXAVAR®, BAY43-9006, Bayer Labs.), and gefitinib (IRESSA®, Astrazeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, especially calicheamicin gamma11 and calicheamicin omega11 (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine (XELODA®, Roche); and pharmaceutically acceptable salts, acids or derivatives of any of the above.

The term "linker" as used herein means a chemical moiety comprising or derived from a group of atoms that is covalently attached to a targeting agent, such as an antibody, and that is also covalently attached to a cytotoxic moiety. Linkers include compounds comprising or derived from divalent radicals such as an alkylene, an arylene, a heteroarylene, moieties such as: —(CR2)nO(CR2)n—wherein R2 is independently repeating units of alkyloxy (e.g. polyethylenoxy, PEG, polymethyleneoxy) and alkylamino (e.g. polyethyleneamino, polyetheramines such as Jeffamine™) and n is independently ≥1, in particular n may be 1 to 15; compounds including the linkers described in Example 1, N-succinimidyl 4-(maleimidomethyl)cyclohexanecarboxylate (SMCC) and N-succinimidyl 4-(2-pyridyldithio)butanoate (SPDB); and diacid ester and amides including succinate, succinamide, diglycolate, malonate, and caproamide as well as peptides, such as but not limited to repeating units of G, A and C (for example up to 10) with one or more lys residues or other suitable chemical groups for linking to a targeting agent and a cytotoxic moiety. The linker is optionally C1-30 alkylene, unsubstituted or substituted with one or more substituents, and/or optionally interrupted with one or more heteromoieties independently selected from O, S, NR1, and/or optionally interrupted with one or more of C(O) and C(S), wherein R1 is independently selected from H, and C1-6 alkyl. The linker can comprise a non-cleavable (stable linker) or cleavable unit (labile linker) such as a peptide bond or a disulfide bond. The linker can be conjugated to the targeting agent and/or the cytotoxic moiety via reactive functional groups.

The term "alkyl" as used herein, whether it is used alone or as part of another group, means straight or branched chain, saturated alkyl groups. The number of carbon atoms that are possible in the referenced alkyl group are indicated by the numerical prefix "$C_{n1-n2}$". For example, the term $C_{1-6}$alkyl means an alkyl group having 1, 2, 3, 4, 5 or 6 carbon atoms.

The term "alkylene" as used herein, whether it is used alone or as part of another group, means straight or branched chain, saturated alkylene group; that is a saturated carbon chain that contains substituents on two of its ends. The number of carbon atoms that are possible in the referenced alkylene group are indicated by the numerical prefix "$C_{n1-n2}$". For example, the term $C_{4-20}$alkylene means an alkylene group having 4, 5, 6, 7, 8, 9, 10, 11, 12, 13, 14, 15, 16, 17, 18, 19 or 20 carbon atoms.

The term "subject" as used herein includes all members of the animal kingdom including mammals, and suitably refers to humans.

The term "pharmaceutically acceptable carrier" as used herein includes essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N,N,N-trimethylammonium chloride (DOTMA), diolesylphosphotidyl-ethanolamine (DOPE), and liposomes. Such compositions should contain a therapeutically effective amount of the conjugate together with a suitable amount of carrier so as to provide the form for direct administration to the subject.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "consisting" and its derivatives, as used herein, are intended to be closed ended terms that specify the presence of stated features, elements, components, groups, integers, and/or steps, and also exclude the presence of other unstated features, elements, components, groups, integers and/or steps.

Further, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

More specifically, the term "about" means plus or minus 0.1 to 50%, 5-50%, or 10-40%, 10-20%, 10%-15%, preferably 5-10%, most preferably about 5% of the number to which reference is being made.

As used in this specification and the appended claims, the singular forms "a", "an" and "the" include plural references unless the content clearly dictates otherwise. Thus for example, a composition containing "a compound" includes a mixture of two or more compounds. It should also be noted that the term "or" is generally employed in its sense including "and/or" unless the content clearly dictates otherwise.

The definitions and embodiments described in particular sections are intended to be applicable to other embodiments herein described for which they are suitable as would be understood by a person skilled in the art.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

Further, the definitions and embodiments described in particular sections are intended to be applicable to other embodiments herein described for which they are suitable as would be understood by a person skilled in the art. For example, in the following passages, different aspects of the invention are defined in more detail.

II. Conjugates and Methods

Accordingly the disclosure provides in one aspect a conjugate comprising:
  a. a targeting agent that specifically binds a non-transmembrane target antigen, wherein the target antigen is secreted by cancer cells;
  b. a cytotoxic moiety, optionally linked directly or indirectly to the targeting agent;
  c. and, optionally, a linker linking the targeting agent and cytotoxic moiety.

In certain embodiments, the target antigens utilize active, receptor-mediated re-internalization of the target antigen bound by the antibody-drug conjugate.

In one embodiment, a conjugate is provided comprising a targeting agent, a cytotoxic moiety, and, optionally, a linker linking the targeting agent and cytotoxic moiety. The targeting agent is an entity that specifically binds to a non-transmembrane target antigen, wherein the target antigen is secreted by cancer cells. In an embodiment, the targeting agent is a binding protein that specifically binds the target antigen. In a preferred embodiment, the conjugate is an antibody-drug conjugate.

In another embodiment, the targeting agent specifically binds a protein target antigen that is a tumor antigen.

In one embodiment, the target antigen is an intracellular protein. In another embodiment, the target antigen is an endocytic or lysosomal protein. In another embodiment, the target antigen is specifically secreted by cancer cells. The secreted target antigen may stay associated with the cancer cells. The secreted target antigen may be internalized or re-internalized by cells by one or more mechanisms including endocytosis, pinocytosis and/or actively internalized by receptor mediated endocytosis.

In one embodiment, the target antigen is internalized by cancer cells more than normal cells. In another embodiment, the target antigen is internalized by cancer cells and not by normal cells.

For example, the amount of cathepsin D detectable in the serum could vary from low ng/mL range to lower concentrations. In contrast, the amount of cathepsin D secreted from tumors or found to accumulate in tumors was demonstrated to be as high as ug levels of cathepsin D per mg of tumor tissues (Capony et al. 1989).

Some cancers have been reported to overexpress and/or secrete cathepsin E, such as gastric cancers or pancreatic cancers.

Lysosomal aspartic proteases include for example human cathepsin D and human cathepsin E.

In an embodiment, the target antigen is a lysosomal protein. In an embodiment, the target antigen is an aspartyl lysosomal enzyme. In an embodiment, the target antigen is human cathepsin D or human cathepsin E. In another embodiment, the target antigen human cathepsin D. In yet another embodiment, the target antigen is or includes human pro-cathepsin D (for example where the targeting agent binds specifically an epitope within amino acids 19 to 64, of the pro-peptide region). In yet another embodiment, the target antigen is or includes human cathepsin D heavy chain (specifically, an epitope within amino acids 169 to 412). In yet another embodiment, the target antigen is or includes human cathepsin D light chain (specifically, an epitope within amino acids 65 to 161).

In one embodiment, the conjugate binds to an epitope of human cathepsin D, outside of regions bound by a cathepsin D receptor, such as the mannose 6 phosphate (M6P) receptor, LRP1, or sortilin.

In an embodiment, the conjugate (e.g. via the targeting agent portion thereof) binds an epitope in cathepsin D that excludes amino acids Asn70 and/or Asn199, which are amino acids that can be modified with mannose 6-phosphate and are involved in mannose 6 phosphate receptor internalization. In an embodiment, the conjugate binds an epitope that excludes surrounding residues to Asn70 and/or Asn199 for example up to 3 amino acids N terminus and/or C terminus to Asn70 and/or Asn 199.

In another embodiment, the target antigen is selected from the group consisting of cathepsin A, cathepsin B, cathepsin C, cathepsin D, cathepsin E, cathepsin F, cathepsin G, cathepsin H, cathepsin K, cathepsin L1, cathepsin L2, cathepsin 0, cathepsin S, cathepsin W, cathepsin Z, apolipoprotein E (ApoE), lipoprotein lipase, hepatic lipase, tissue plasminogen activator (tPA), urinary-type plasminogen activator (uPA), Factor IXa, Factor VIIIa, Factor VIIa/TFPI, matrix metalloproteinase (MMPs), such as, MMP-13, MMP-9, Spingolipid activator protein (SAP), Pregnancy Zone Protein, α-2-macroglobulin (α2M), Complement C3, plasminogen activator inhibitor-1 (PAI-1), C1 inhibitor, Antithrombin III, tissue factor pathway inhibitor (TFPI), Heparin cofactor II, α1-Antitrypsin, amyloid precursor protein (APP), Thrombospondin-1, Thrombospondin-2, Lactoferrin, Ras-related proteins (RAPs), and heat shock protein-96 (HSP-96).

In one embodiment, the conjugate binds the tumor antigen through an epitope to form a complex that is capable of being internalized into cells.

This can for example be determined in a reinternalization assay. An example is provided in Example 4. A targeting agent for a target antigen (such as antibody for a specific target antigen) can be conjugated to a pH-responsive fluorescent label, such as the pHrodo Red label, which is a pH-sensitive dye whose spectral (fluorescence) properties change in response to lowering of pH. This can be accomplished using the pHrodo Red succinimidyl (NHS) ester reagent (Molecular Probes, Life Technologies, Carlsbad, Calif., US), by contacting this reagent with the targeting agent and then purifying the pHrodo Red-conjugate by removing the unreacted label. The pHrodo Red-conjugate can then be added to cultured cells known to secrete the target antigen, for example MCF-7 cells in the case of cathepsin D, incubated, and the fluorescence of the culture in the 560 nm can be measured to determine the extent of pHrodo Red-conjugate internalization. Upon internalization of the dye-containing conjugate into cells and exposure to low pH endosomal and lysosomal intracellular compartments, the fluorescence emission of the dye in the 560 nm range increases. Thus, the extend of pHrodo Red-conjugate internalization can be relatively quantified via the measurement of increase in fluorescence in the 560 nm range in the cell culture. This can be assessed with a multimodal plate reader or by flow cytometry.

In another embodiment, the conjugate also comprises a cell-penetrating peptide (CPP) to increase its internalization into cells. For example, the cell penetrating portion of the Human Immunodeficiency Virus (HIV)-derived Tat protein known as the Tat peptide. Another example would be the CADY cell penetrating peptide. In an embodiment, the CPP is fused in-frame to the C-terminus of the targeting protein or any subunit thereof.

In embodiments in which the conjugate includes a linker, the linker may be stable or labile. In an embodiment, the stable linker is N-succinimidyl 4-(maleimidomethyl) cyclohexanecarboxylate (SMCC) or a derivative thereof. In another embodiment, the labile linker is N-succinimidyl-3-(2-pyridyldithio)propionate (SPDP) or a derivative thereof. In another embodiment, the labile linker is N-succinimidyl 4-(2-pyridyldithio)butanoate (SPDB). This labile linker can be cleaved for example by the action of reducing agents, such as those found in the cell cytosol or enzymes in the cell. Labile linkers may produce increased efficacy in some embodiments, for example where the internalization results in recycling of the conjugate to the cell surface or in cases where there is a failure in trafficking of the conjugate to the lysosomal compartment following internalization. For example, the linker can comprise a macromolecule such as a peptide that comprises an enzyme cleavage site (e.g. a protease cleavage site for peptide macromolecules). For example, the linker can be a dipeptide linker, such as a valine-citrulline (val-cit) or a phenylalanine-lysine (phe-lys) linker. In one aspect of the embodiment, the labile linker is a self-immolating linker. For example, the linker can comprise a para-aminobenzyloxycarbonyl (PAB) moiety or derivative thereof. In one aspect of the embodiment, the labile linker is cleavable intracellularly, for example cleavable according to pH, reducing agents, enzymes present intracellularly or in an intracellular compartment such as the lysosome, etc. In an embodiment, the linker can be derived from a cross-linking reagent selected from the group consisting of N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)2-sulfo-butanoate (sulfo-SPDB), N-succinimidyl iodoacetate (SIA), N-succinimidyl(4-iodoacetyl)aminobenzoate (SIAB), N-succinimidyl bromoacetate (SBA), N-succinimidyl 3-(bromoacetamido)propionate (SBAP), maleimide PEG NHS, N-succinimidyl 4-(maleimidomethyl) cyclohexanecarboxylate (SMCC), N-succinimidyl-4-(N-maleimidomethyl)-cyclohexane-1-carboxy-(6-amidocaproate) (LC-SMCC), N-sulfosuccinimidyl 4-(maleimidomethyl) cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CXI-1), K-maleimidoundecanoic acid N-succinimidyl ester (KMUA), γ-maleimidobutyric acid N-succinimidyl ester (GMBS), ε-maleimidcaproic acid N-hydroxysuccinimide ester (EMCS), m-maleimidobenzoyl-N-hydroxysuccinimide ester (MBS), N-(a-maleimidoacetoxy)-succinimide ester (AMAS), succinimidyl-6-(P-maleimidopropionamido) hexanoate (SMPH), N-succinimidyl 4-(p-maleimidophenyl)-butyrate (SMPB), or N-(p-maleimidophenyl)isocyanate (PMPI).

In one embodiment, the conjugate comprises a cytotoxic moiety selected from the group consisting of a microtubule stabilizer, a microtubule destabilizer, an auristatin, a dolastatin, a maytansinoid, a tubulysin, a cryptophycins, a methionine aminopeptidase, a calicheamicin, an inhibitor of nuclear export of proteins CRM1, a DPPIV inhibitor, proteasome inhibitors, inhibitors of phosphoryl transfer reactions, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder, a DHFR inhibitor, a pro-apoptotic agent, a Bcl2 inhibitor, an MCL1 inhibitor, a HSP90 inhibitor, an IAP inhibitor, and an mTor inhibitor, N(2')-deacetyl-N(2')-(3-mercapto-1-oxopropyl)-maytansine (DM1), or N(2')-deacetyl-N2-(4-mercapto-4-methyl-1-oxopentyl)-maytansine (DM4).

In one embodiment, the conjugate comprises a cytotoxic moiety selected from the group consisting of a microtubule stabilizer, a microtubule destabilizer, an auristatin, a dolastatin, a maytansinoid, a tubulysin, a cryptophycins, a methionine aminopeptidase, a calicheamicin, an inhibitor of nuclear export of proteins CRM1, a DPPIV inhibitor, proteasome inhibitors, inhibitors of phosphoryl transfer reactions, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder, a DHFR inhibitor, a pro-apoptotic agent, a Bcl2 inhibitor, an MCL1 inhibitor, a HSP90 inhibitor, an IAP inhibitor, and an mTor inhibitor, N(2')-deacetyl-N(2')-(3-mercapto-1-oxopropyl)-maytansine (DM1), or N(2')-deacetyl-N(2')-(4-mercapto-4-methyl-1-oxopentyl)-maytansine (DM4).

In preferred embodiments, the conjugate comprises the N-succinimidyl 4-(2-pyridyldithio)butanoate (SPDB) linker and the N(2')-deacetyl-N(2')-(4-mercapto-4-methyl-1-oxopentyl)-maytansine (DM4) cytotoxic moiety, known as SPDB-DM4. The SMCC linker is particularly useful for creating stable linkage of the cytotoxic moiety to the targeting agent, such as an antibody. In other preferred embodiments, the conjugate comprises the N-succinimidyl 4-(maleimidomethyl)cyclohexanecarboxylate (SMCC) linker and the N(2')-deacetyl-N(2')-(3-mercapto-1-oxopropyl)-maytansine (DM1) conjugate, known as SMCC-DM1. DM1 and DM4 cytotoxic moieties are based on the complex structure of the natural molecule, maystansine. Several forms of maytansinoids that retain their cytotoxic activity are useful.

In one embodiment, the targeting agent is selected from a binding protein and a nucleic acid, such as DNA, RNA or an aptamer. In one aspect of this embodiment, the binding protein is selected from an antibody, affimer and receptor. In one aspect of this embodiment, the binding protein is an antibody, wherein the antibody is selected from the group consisting of a monoclonal antibody, a polyclonal antibody, an antibody fragment, a chimeric antibody, a humanized antibody, a human antibody, a single chain Fv (scFv), a nanobody, a single-domain antibody (sdAb), and an antibody fragment such as an Fab fragment, and an F(ab')2 fragment.

In a preferred embodiment, the targeting agent is a monoclonal antibody, optionally a chimeric monoclonal antibody.

Also provided in another embodiment, for conjugates where the cytotoxic moiety is a proteinaceous toxin, and/or for conjugates comprising a proteinaceous linker, is a nucleic acid encoding the conjugate or part thereof, eg. targeting agent (e.g. binding protein or antibody) and linker, linker and proteinaceous cytotoxic moiety.

Also provided in another aspect is a composition comprising the conjugate described herein or a nucleic acid encoding said conjugate or part thereof, optionally in combination with a carrier, diluent or excipient. In an embodiment the carrier diluent or excipient is a pharmaceutically acceptable.

In some embodiments, the composition is suitable for intravenous, intramuscular, subcutaneous, parenteral, spinal or epidermal administration.

In an embodiment, the composition is a pharmaceutical composition.

Another aspect includes a method of delivering a cytotoxin selectively to cancer cells, the method comprising contacting the cell with a conjugate described herein or a composition comprising said conjugate.

Also provided are uses of the conjugate and composition comprising said conjugate for delivering a cytotoxin selectively to cancer cells.

In an embodiment, the cancer cells to be targeted are in a subject and the cells are contacted by administering the conjugate or composition to the subject in need thereof.

Also provided in another aspect is a method or use for treating cancer.

Accordingly in an embodiment the method of treating cancer comprises administering to a subject in need thereof an effective amount of the conjugate described herein or a composition comprising said conjugate.

In one embodiment, the conjugate or a compositions comprising the conjugate is administered to a subject in need thereof optionally in combination with another therapeutic agent.

In one embodiment, a method of treating cancer, comprising administering the conjugate to a subject in need thereof, is provided. In one aspect, the method comprises selectively delivering the conjugate to cancer cells comprising:
   systemically or locally administrating the conjugate to the subject;
   wherein the subject comprises cancer cells secreting the target antigen, and normal cells lacking secretion or secreting less of the target antigen, compared to said cancer cells;
   and wherein the cancer cells internalize the target antigen: conjugate complex.

In one aspect of the embodiment, the subject is a human. In one aspect, the subject has metastasis.

In an embodiment, between 1 µg/kg and 20 mg/kg (0.001-20 mg/kg dose) of the conjugate per kilogram weight of the subject is administered to the subject optionally by one or more separate administrations, or via continuous infusion. Other dosage regimens may be useful. For example, administering a single large dose, followed by multiple lower, maintenance doses. For repeated administrations, the treatment administration is sustained until the desired level of suppression of cancer or associated symptoms is achieved.

In one aspect of the embodiment, the conjugate is administered by injection. In one aspect of the embodiment, the cancer is a solid tumor. In certain aspects, the cancer is selected from the group consisting of breast cancer, triple-negative breast cancer, prostate cancer, ovarian cancer, endometrial cancer, non-small cell lung cancer (NSCLC), hepatocellular carcinoma (HCC), head & neck squamous cell carcinoma (HNSCC), bladder cancer, pancreatic cancer, glioblastoma multiforme (GBM), small-cell lung cancer, melanoma or renal cell carcinoma. In one aspect, the cancer is breast cancer. In another aspect, the cancer is a triple-negative breast cancer.

In another embodiment, a method of making an antibody-drug conjugate is provided, comprising either:
   a. reacting the targeting agent with a linker precursor reagent to form a targeting agent-linker conjugate containing between 1 and 20 linker molecules;
   b. reacting the targeting agent-linker conjugate with the cytotoxic moiety to form the conjugate, the conjugate containing 1-20 molecules of the cytotoxic moiety; or
   a. reacting the cytotoxic moiety with a linker precursor reagent to form a linker-cytotoxic moiety conjugate;
   b. reacting the linker-cytotoxic moiety conjugate with the targeting agent to form the conjugate, the conjugate containing 1-20 linker-cytotoxic moiety molecules.

In one embodiment, the method of using the conjugate is provided by parenterally administering an effective amount of the conjugate. Suitable routes of administration include intravenous, subcutaneous, intramuscular, intracranial, intraorbital, intraventricular, intracapsular, intraspinal, intracisternal, intraperitoneal, intranasal, aerosol, ophthalmic, pulmonary, and oral.

In some embodiments, a pharmaceutical composition is provided, comprising an effective amount of the conjugate, pharmaceutically acceptable salt or solvate thereof, and a pharmaceutically acceptable carrier, diluent or excipient. The conjugate can be administered in unit dosage form, with suitable dosage forms being for example 10 mgs, 50 mgs, 100 mgs, 200 mgs, 300 mgs, and 500 mgs. The drug can be formulated in single use vials at a concentration of between 1 and as much as 20 mg/mL. Suitable vehicles include for example saline.

In another embodiment, a method for selecting a cancer biomarker as a target antigen for preparing the conjugate is provided, comprising:
   a. testing non-cancer cells for a candidate antigen to determine if it is intracellular and/or normally non-secreted by non-cancer cells;
   b. testing cancer cells for the candidate antigen to determine if it is secreted by cancer cells;
   c. if the target antigen is secreted by cancer cells in an amount greater than the non-cancer cells, testing cancer cells for the candidate antigen to determine if it can be re-internalized by cancer cells; and
   d. identifying a target antigen that is secreted by cancer cells in an amount greater than non-cancer cells and is reinternalizable by cancer cells as a candidate target intracellular tumor antigen.

Standard existing biochemical and molecular biology techniques can be used to determine whether an antigen is intracellular, secreted, and internalized by cells, such as flow cytometry, Western blot and other immunological detection methods.

In an embodiment, the non-cancer cells of step a) and the cancer cells of step b) are each cultured in culture media for a period of time and the culture media of each is measured for the level of target antigen.

In an embodiment, mass spectrometry is used to measure the level of the target antigen.

In another embodiment, a diagnostic reagent binding to the protein target of the conjugate is provided. In one aspect, the diagnostic reagent comprises the targeting agent of the conjugate. In another aspect, a companion diagnostic kit is provided based on the protein target of the conjugate.

In one embodiment, the antibody-drug conjugate target antigen can include, non-exhaustively, cathepsins, such as cathepsin D, ApoE, lipoprotein lipase, hepatic lipase, tPA, uPA, Factor IXa, Factor VIIIa, Factor VIIa/TFPI, MMPs, such as, MMP-13, MMP-9, Spingolipid activator protein (SAP), Pregnancy Zone Protein, α2M, Complement C3, PAI-1, C1 inhibitor, Antithrombin III, TFPI, Heparin cofactor II, α1-Antitrypsin, APP, Thrombospondin-1, Thrombospondin-2, Lactoferrin, RAP, HSP-96 (Herz and Strickland 2001).

In one embodiment, the antibody-drug conjugate may contain a cell-penetrating peptide (CPP) to increase its ability to internalize into cells.

In certain embodiments, a linker-cytotoxic compound is conjugated to a target protein. In an embodiment, the linker-cytotoxic moiety compound used to conjugate to a binding protein is a compound or a derivative or a salt or solvate thereof:

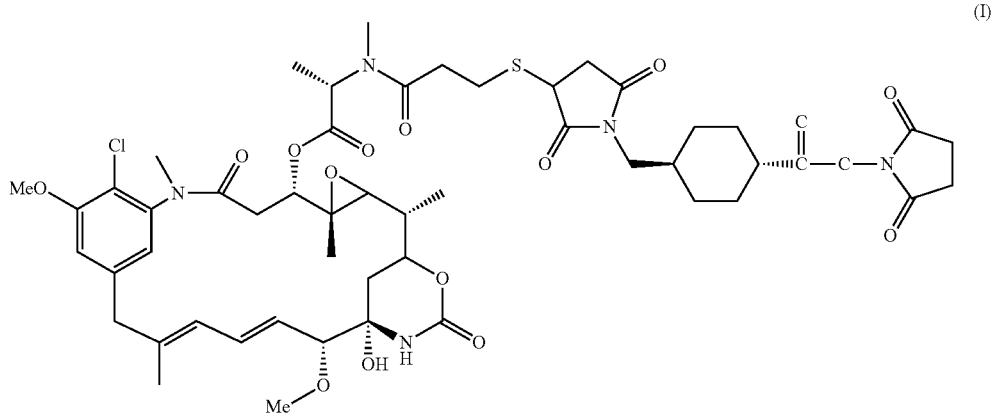 [SMILES: C=C(CN1C(=O)CCC1=O)[C@H]1CC[C@H](CN2C(=O)CC(SCCC(=O)N(C)[C@@H](C)C(=O)O[C@H]3CC(=O)N(C)c4cc(cc(OC)c4Cl)C/C(C)=C/C=C/[C@@H](OC)[C@@]4(O)CC(OC(=O)N4)[C@@H](C)C4O[C@]43C)C2=O)CC1]

(I)

In another embodiment, the linker-cytotoxic moiety compound that is used to conjugate to a binding protein is a compound of formula II or a derivative or a salt or solvate thereof:

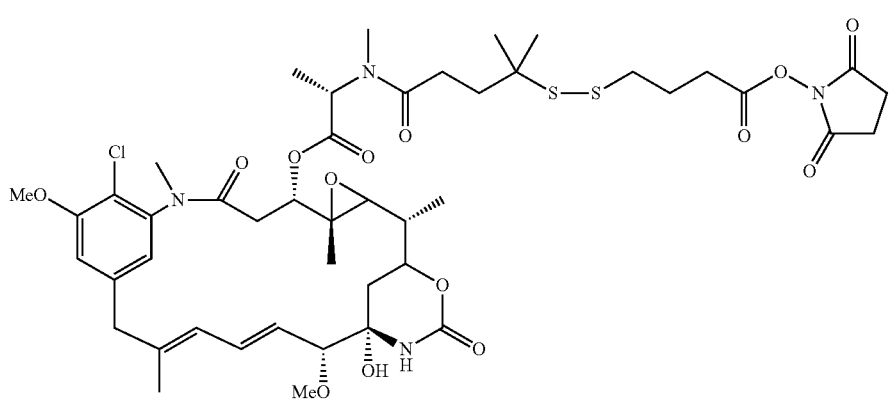

(II)

Figure 9:
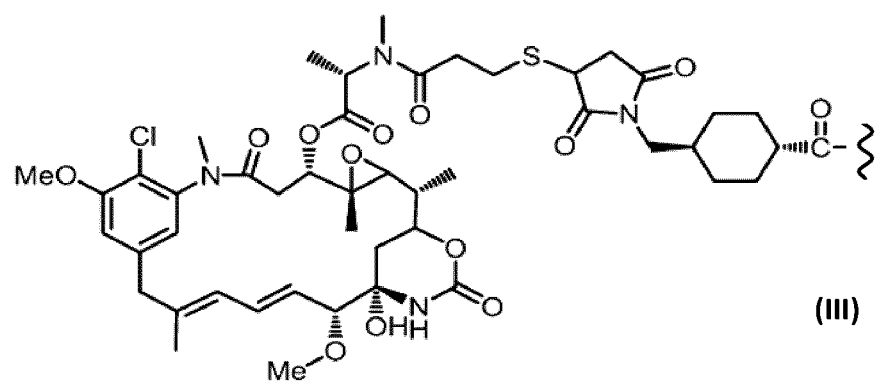
FIG. 9 is a schematic depicting exemplary conjugates and toxic moiety linkers.
Figure 9:
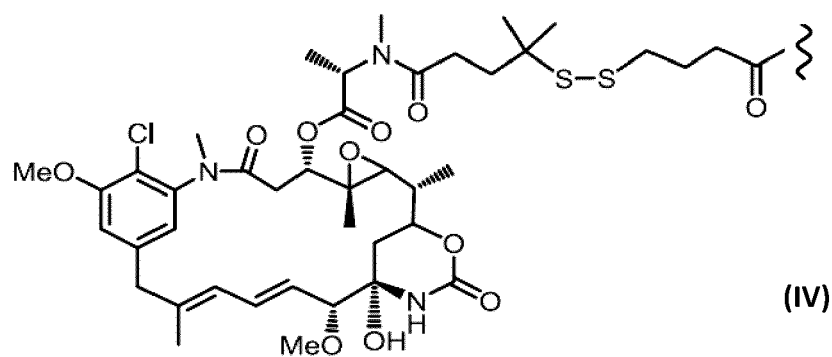
Figure 9:
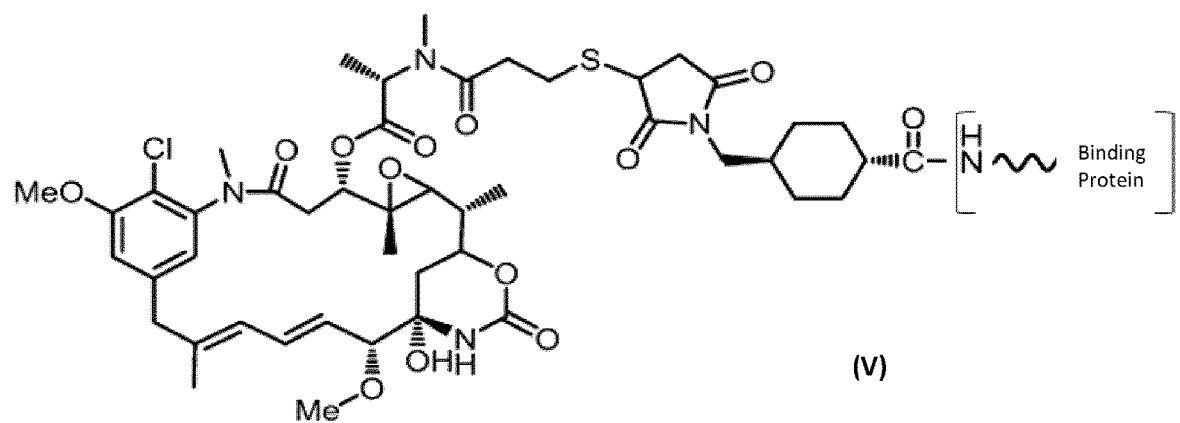
Figure 9:
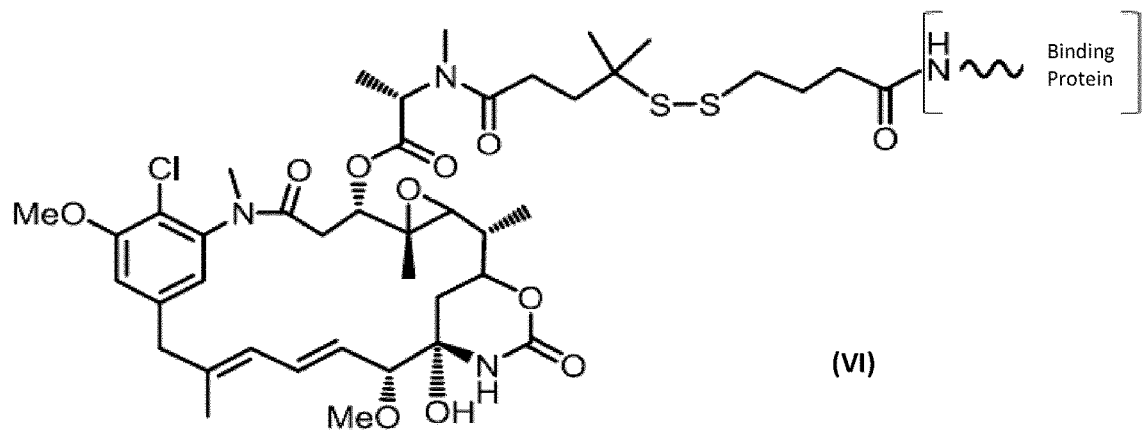

Once reacted with the binding protein, the NHS group is lost. As shown in FIG. 9, the cytotoxic moiety linker component of the conjugate can in an embodiment, have the structure of formula III or IV. In an embodiment, the conjugate can have the structure as shown in formula V or VI.

In a preferred embodiment, the synthesis of the conjugate of the targeting agent, in this example, an antibody, with the SMCC-DM1 and SPDB-DM4 linker-cytotoxic moieties can be accomplished by the following steps:

Exchanging buffer (if in buffer) or suspending antibody into 50 mM potassium phosphate/50 mM sodium chloride/2 mM EDTA, pH 6.5. The concentration of antibody can be measured by absorbance at 280 nm. (The antibody will be reacted with 7.5-fold molar excess SMCC or SPDB linker and purified by Sephadex G25 resin before conjugation to DM1 or DM4.)

A 20 mM solution of SMCC or SPDB is prepared in DMSO. The concentration of the stock solution can be verified by absorbance at 302 nm. A 10 mM solution of DM1 or DM4 (in free thiol form) can be prepared in dimethylamine (DMA). The concentration of the solution can be verified by measuring the absorbance of its dilutions in ethanol at 280 nm. The concentration of free —SH in the stock DM1/DM4 preparations can be measured using Ellman's reagent (DTNB). The antibody is then modified using a 7.5-fold molar excess of SMCC/SPDB at 20 mg/mL concentration of antibody.

The reaction is carried out in 50 mM potassium phosphate/50 mM sodium chloride/2 mM EDTA, pH 6.5 (95% v/v) with DMSO (5% v/v) for 2 hours at room temperature with stirring. The antibody-SMCC or antibody-SPDB precursor is then gel-filtered through a 1.5×4.9 cm pre-packed column of Sephadex G25 resin equilibrated in 50 mM potassium phosphate/50 mM sodium chloride/2 mM EDTA, pH 6.5. The antibody-SMCC or antibody-SPDB precursor is then reacted with a 1.7-fold excess of DM1 or DM4 over linker (assuming an average of 5 linkers per antibody). The reaction is carried out at 10 mg/mL concentration of antibody in 50 mM potassium phosphate/50 mM sodium chloride/2 mM EDTA, pH 6.5 (94% v/v) with DMA (6% v/v). After the addition of DM1 or DM4, the reaction is incubated at room temperature for 16.5 hours with stirring. The conjugation reaction mixture is then gel-filtered through a 1.5×4.9 cm pre-packed column of Sephadex G25 resin equilibrated in phosphate buffered saline (PBS), pH 6.5. The number of DM1 or DM4 molecules linked per mole of antibody (drug:antibody ratio) can be determined by measuring absorbance at 252 nm and 280 nm. The resulting conjugate is analyzed for binding to target antigen and cytotoxicity.

The following non-limiting examples are illustrative of the present disclosure:

EXAMPLES

Example 1

Synthesis and Characterization of Antibody-Drug Conjugate: Anti-Cathepsin D-SMCC-DM1 (IMB-101)

Mouse anti-human cathepsin D antibody was obtained from a commercial source (R&D Systems, Minneapolis, Minn., MAB1014, Clone 185111, MW 150 kDa), and recognizes human cathepsin D by Western blot and native protein by direct ELISA. The antibody was reconstituted into sterile phosphate-buffered saline (pH 7.2) to a concentration of 0.5 mg/ml and was then further dialyzed against sterile PBS. The linker, N-succinimidyl 4-(maleimidomethyl) cyclohexanecarboxylate (SMCC) was supplied already coupled to the cytotoxic moiety, maytansine DM1, as SMCC-DM1 and was obtained from a commercial source (Concortis, San Diego, Calif., MW 1071.39) and was used for direct coupling to the primary amines of the antibody using N-hydroxysuccinimide (NHS) chemistry. The SMCC-DM1 was resuspended in dry DMSO to a concentration of 1 mg/ml. The pH of the solutions was confirmed to be between pH 7.2 and 7.5. An appropriate volume of the SMCC-DM1 solution was added to the antibody solution to achieve a final molar ratio of 20:1 of SMCC-DM1 to antibody, and the mixture was reacted on ice for 2 hours and then 1 hour at room temperature. The resulting mixture was extensively dialyzed against PBS (pH 7.2) (between 5-10 buffer exchanges) to remove unreacted or unbound SMCC-DM1. Alternatively, clean up can be accomplished by repeated desalting or diafiltration using a centrifugal ultrafiltration device, such as, for example, the Amicon Ultra-0.5 (50K or 100K MWCO) ultrafiltration device (Millipore, Billerica, Mass., US) (between 4 and 7 buffer exchanges with PBS (pH7.2), as needed). The concentration of the resulting product was determined by the Pierce BCA protein assay (Burlington, ON). The drug:antibody ratio was determined by measuring the absorbance of the solution at 252 nm and 280 nm, assuming antibody MW of approximately 150 kDa, and antibody extinction coefficient of 87,360 $M^{-1}$ $cm^{-1}$ at 252 nm and 224,000 $M^{-1}$ $cm^{-1}$ at 280 nm, and linker-cytotoxic moiety extinction coefficient of 28,044 $M^{-1}$ $cm^{-1}$ at 252 nm and 5,700 $M^{-1}$ $cm^{-1}$ at 280 nm.

The structure of SMCC-DM1 reagent using for making the ADC is as following:

Synthesis and Characterization of Antibody-Drug Conjugate: Anti-Cathepsin D-SPDB-DM4 (IMB-102)

Mouse anti-human cathepsin D antibody was obtained from a commercial source (R&D Systems, Minneapolis, Minn., MAB1014, Clone 185111, MW 150 kDa), and recognizes human cathepsin D by Western blot and native protein by direct ELISA. The antibody was reconstituted into sterile phosphate-buffered saline (pH 7.2) to a concentration of 0.5 mg/ml and was then further dialyzed against sterile PBS. The linker, was supplied already coupled to the cytotoxic moiety, maytansine DM4, as SPDB-DM4 and was obtained from a commercial source (Concortis, San Diego, Calif., MW 994.35) and was used for direct coupling to the primary amines of the antibody using N-hydroxysuccinimide (NHS) chemistry. The SPDB-DM4 was resuspended in dry DMSO to a concentration of 1 mg/ml. The pH of the solutions was confirmed to be between pH 7.2 and 7.5. An appropriate volume of the SPDB-DM4 solution was added to the antibody solution to achieve a final molar ratio of 20:1 of SPDB-DM4 to antibody, and the mixture was reacted on ice for 2 hours and then 1 hour at room temperature. The resulting mixture was extensively dialyzed against PBS (pH 7.2) (between 5-10 buffer exchanges) to remove unreacted or unbound SPDB-DM4. Alternatively, clean up can be accomplished by repeated desalting or diafiltration using a centrifugal ultrafiltration device, such as, for example, the Amicon Ultra-0.5 (50K or 100K MWCO) ultrafiltration device (Millipore, Billerica, Mass., US) (between 4 and 7 buffer exchanges with PBS (pH7.2), as needed). The concentration of the resulting product was determined by the Pierce BCA protein assay (Burlington, ON). The drug:antibody ratio was determined by measuring the absorbance of the solution at 252 nm and 280 nm, assuming antibody MW of approximately 150 kDa, and antibody extinction coefficient of 87,360 $M^{-1}$ $cm^{-1}$ at 252 nm and 224,000 $M^{-1}$ $cm^{-1}$ at 280 nm, and linker-cytotoxic moiety extinction coefficient of 28,044 $M^{-1}$ $cm^{-1}$ at 252 nm and 5,700 $M^{-1}$ $cm^{-1}$ at 280 nm.

The structure of SPDB-DM4 reagent used for making the ADC is as following:

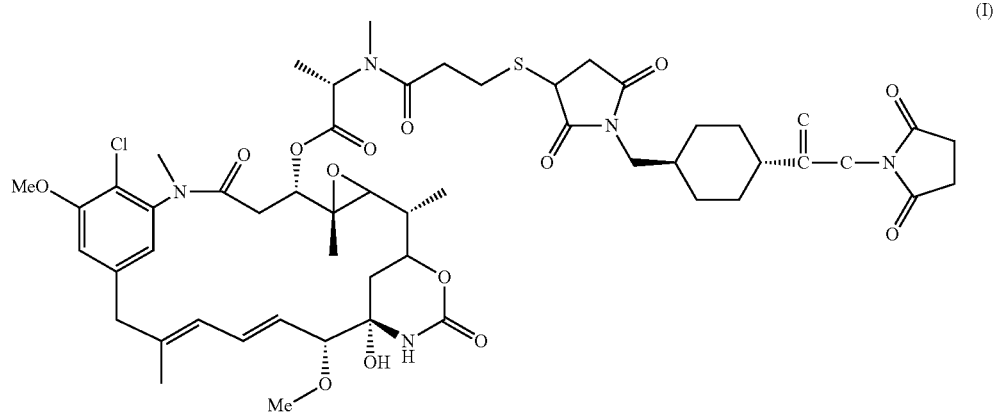 [SMILES: C=C(CN1C(=O)CCC1=O)[C@H]1CC[C@H](CN2C(=O)CC(SCCC(=O)N(C)[C@@H](C)C(=O)O[C@H]3CC(=O)N(C)c4cc(cc(OC)c4Cl)C/C(C)=C/C=C/[C@@H](OC)[C@@]4(O)CC(OC(=O)N4)[C@@H](C)C4O[C@]43C)C2=O)CC1]

(I)

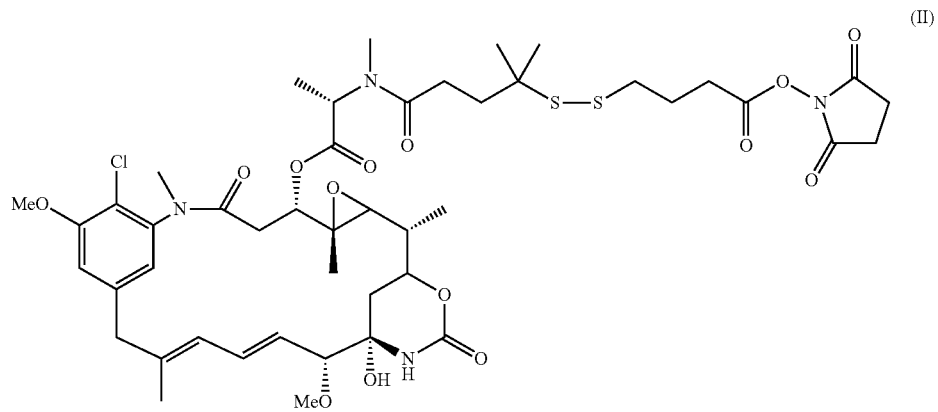 [SMILES: COc1cc2cc(c1Cl)N(C)C(=O)C[C@H](OC(=O)[C@H](C)N(C)C(=O)CCC(C)(C)SSCCCC(=O)ON1C(=O)CCC1=O)[C@]1(C)OC1[C@H](C)C1C[C@@](O)(NC(=O)O1)[C@H](OC)/C=C/C=C(\C)C2]

Synthesis and Characterization of Antibody-Drug Conjugate: Anti-EGFR-SMCC-DM1 (IMB-701)

Mouse anti-human EGFR antibody was obtained from a commercial source (R&D Systems, Minneapolis, Minn., MAB1095, Clone 102618, MW 150 kDa). The antibody was reconstituted into sterile phosphate-buffered saline (pH 7.2) to a concentration of 0.5 mg/ml and was then further dialyzed against sterile PBS. The linker, was supplied already coupled to the cytotoxic moiety, maytansine DM1, as SMCC-DM1 and was obtained from a commercial source (Concortis, San Diego, Calif., MW 1071.39) and was used for direct coupling to the primary amines of the antibody using N-hydroxysuccinimide (NHS) chemistry. The SMCC-DM1 was resuspended in dry DMSO to a concentration of 1 mg/ml. The pH of the solutions was confirmed to be between pH 7.2 and 7.5. An appropriate volume of the SMCC-DM1 solution was added to the antibody solution to achieve a final molar ratio of 20:1 of SMCC-DM1 to antibody, and the mixture was reacted on ice for 2 hours and then 1 hour at room temperature. The resulting mixture was extensively dialyzed against PBS (pH 7.2) (between 5-10 buffer exchanges) to remove unreacted or unbound SMCC-DM1. Alternatively, clean up can be accomplished by repeated desalting or diafiltration using a centrifugal ultrafiltration device, such as, for example, the Amicon Ultra-0.5 (50K or 100K MWCO) ultrafiltration device (Millipore, Billerica, Mass., US) (between 4 and 7 buffer exchanges with PBS (pH7.2), as needed). The concentration of the resulting product was determined by the Pierce BCA protein assay (Burlington, ON). The drug:antibody ratio was determined by measuring the absorbance of the solution at 252 nm and 280 nm, assuming antibody MW of approximately 150 kDa, and antibody extinction coefficient of 87,360 $M^{-1}$ $cm^{-1}$ at 252 nm and 224,000 $M^{-1}$ $cm^{-1}$ at 280 nm, and linker-cytotoxic moiety extinction coefficient of 28,044 $M^{-1}$ $cm^{-1}$ at 252 nm and 5,700 $M^{-1}$ $cm^{-1}$ at 280 nm.

Synthesis and Characterization of Antibody-Drug Conjugate: Anti-EGFR-SPDB-DM4 (IMB-702)

Mouse anti-human EGFR antibody was obtained from a commercial source (R&D Systems, Minneapolis, Minn., MAB1095, Clone 102618, MW 150 kDa). Mouse anti-human cathepsin D antibody was obtained from a commercial source (R&D Systems, Minneapolis, Minn., MAB1014, Clone 185111, MW 150 kDa), and recognizes human cathepsin D by Western blot and native protein by direct ELISA. The antibody was reconstituted into sterile phosphate-buffered saline (pH 7.2) to a concentration of 0.5 mg/ml and was then further dialyzed against sterile PBS. The linker, was supplied already coupled to the cytotoxic moiety, maytansine DM4, as SPDB-DM4 and was obtained from a commercial source (Concortis, San Diego, Calif., MW 994.35) and was used for direct coupling to the primary amines of the antibody using N-hydroxysuccinimide (NHS) chemistry. The SPDB-DM4 was resuspended in dry DMSO to a concentration of 1 mg/ml. The pH of the solutions was confirmed to be between pH 7.2 and 7.5. An appropriate volume of the SPDB-DM4 solution was added to the antibody solution to achieve a final molar ratio of 20:1 of SPDB-DM4 to antibody, and the mixture was reacted on ice for 2 hours and then 1 hour at room temperature. The resulting mixture was extensively dialyzed against PBS (pH 7.2) (between 5-10 buffer exchanges) to remove unreacted or unbound SPDB-DM4. Alternatively, clean up can be accomplished by repeated desalting or diafiltration using a centrifugal ultrafiltration device, such as, for example, the Amicon Ultra-0.5 (50K or 100K MWCO) ultrafiltration device (Millipore, Billerica, Mass., US) (between 4 and 7 buffer exchanges with PBS (pH7.2), as needed). The concentration of the resulting product was determined by the Pierce BCA protein assay (Burlington, ON). The drug:antibody ratio was determined by measuring the absorbance of the solution at 252 nm and 280 nm, assuming antibody MW of approximately 150 kDa, and antibody extinction coefficient of 87,360 $M^{-1}$ $cm^{-1}$ at 252 nm and 224,000 $M^{-1}$ $cm^{-1}$ at 280 nm, and linker-cytotoxic moiety extinction coefficient of 28,044 $M^{-1}$ $cm^{-1}$ at 252 nm and 5,700 $M^{-1}$ $cm^{-1}$ at 280 nm.

Synthesis and Characterization of Antibody-Drug Conjugate: Isotype Control-SMCC-DM1 (IMB-991)

The mouse IgG1-kappa isotype control antibody was obtained from a commercial source. (Sigma, M9035, Clone MOPC-31C, MW 150 kDa) and was dialyzed against sterile phosphate-buffered saline (PBS), pH 7.2. The linker, was supplied already coupled to the cytotoxic moiety, maytansine DM1, as SMCC-DM1 and was obtained from a commercial source (Concortis, San Diego, Calif., MW 1071.39) and was used for direct coupling to the primary amines of the antibody using N-hydroxysuccinimide (NHS) chemistry. The SMCC-DM1 was resuspended in dry DMSO to a concentration of 1 mg/ml. The pH of the solutions was confirmed to be between pH 7.2 and 7.5. An appropriate volume of the SMCC-DM1 solution was added to the antibody solution to achieve a final molar ratio of 20:1 of SMCC-DM1 to antibody, and the mixture was reacted on ice for 2 hours and then 1 hour at room temperature. The resulting mixture was extensively dialyzed against PBS (pH 7.2) (between 5-10 buffer exchanges) to remove unreacted or unbound SMCC-DM1. Alternatively, clean up can be accomplished by repeated desalting or diafiltration using a centrifugal ultrafiltration device, such as, for example, the Amicon Ultra-0.5 (50K or 100K MWCO) ultrafiltration device (Millipore, Billerica, Mass., US) (between 4 and 7 buffer exchanges with PBS (pH7.2), as needed). The concentration of the resulting product was determined by the Pierce BCA protein assay (Burlington, ON). The drug:antibody ratio was determined by measuring the absorbance of the solution at 252 nm and 280 nm, assuming antibody MW of approximately 150 kDa, and antibody extinction coefficient of 87,360 $M^{-1}$ $cm^{-1}$ at 252 nm and 224,000 $M^{-1}$ $cm^{-1}$ at 280 nm, and linker-cytotoxic moiety extinction coefficient of 28,044 $M^{-1}$ $cm^{-1}$ at 252 nm and 5,700 $M^{-1}$ $cm^{-1}$ at 280 nm.

Synthesis and Characterization of Antibody-Drug Conjugate: Isotype Control-SPDB-DM4 (IMB-992)

The mouse IgG1-kappa isotype control antibody was obtained from a commercial source. (Sigma, M9035, Clone MOPC-31C, MW 150 kDa) and was dialyzed against sterile phosphate-buffered saline (PBS), pH 7.2. The linker, was supplied already coupled to the cytotoxic moiety, maytansine DM4, as SPDB-DM4 and was obtained from a commercial source (Concortis, San Diego, Calif., MW 994.35) and was used for direct coupling to the primary amines of the antibody using N-hydroxysuccinimide (NHS) chemistry. The SPDB-DM4 was resuspended in dry DMSO to a concentration of 1 mg/ml. The pH of the solutions was confirmed to be between pH 7.2 and 7.5. An appropriate volume of the SPDB-DM4 solution was added to the antibody solution to achieve a final molar ratio of 20:1 of SPDB-DM4 to antibody, and the mixture was reacted on ice for 2 hours and then 1 hour at room temperature. The resulting mixture was extensively dialyzed against PBS (pH 7.2) (between 5-10 buffer exchanges) to remove unreacted or unbound SPDB-DM4. Alternatively, clean up can be accomplished by repeated desalting or diafiltration using a centrifugal ultrafiltration device, such as, for example, the Amicon Ultra-0.5 (50K or 100K MWCO) ultrafiltration device (Millipore, Billerica, Mass., US) (between 4 and 7 buffer exchanges with PBS (pH7.2), as needed). The concentration of the resulting product was determined by the Pierce BCA protein assay (Burlington, ON). The drug:antibody ratio was determined by measuring the absorbance of the solution at 252 nm and 280 nm, assuming antibody MW of approximately 150 kDa, and antibody extinction coefficient of 87,360 $M^{-1}$ $cm^{-1}$ at 252 nm and 224,000 $M^{-1}$ $cm^{-1}$ at 280 nm, and linker-cytotoxic moiety extinction coefficient of 28,044 $M^{-1}$ $cm^{-1}$ at 252 nm and 5,700 $M^{-1}$ $cm^{-1}$ at 280 nm.

Evaluation of Activity of Antibody-Drug Conjugates Against Human Breast Cancer Cell Lines The MCF-7 (ATCC, Manassas, Va.) and MDA-MB-231 (ATCC, Manassas, Va.) breast cancer cell lines were cultured in Dulbecco's Modified Eagle Medium (DMEM, Sigma-Aldrich, St. Louis, Mo.) supplemented with 10% FBS, 100 units/mL of penicillin, 100 µg/mL of streptomycin, and 2 mM L-glutamine. Between 2,000 and 10,000 cells were seeded per well of a flat-bottom 96-well tissue culture plate, and subsequently incubated with various concentrations of the test articles (conjugates) in culture media for up to 5 days at 37° C., humidified, 5% $CO_2$ incubator. Positive cell killing control was established by a 2-hour pre-treatment of control wells with 10% ethanol in culture media. Viability of the cells remaining after treatment in each well was determined via the MTS cell viability assay (3-(4,5-dimethylthiazol-2-yl)-5-(3-carboxymethoxyphenyl)-2-(4-sulfophenyl)-2H-tetrazolium, inner salt (MTS), Promega, Madison, Wis.) by addition of 20-40 ul of reagent per well. The MTS assay was then incubated between 30 min and 2 hours, and subsequently analyzed by measuring absorbance of each well at 490 nm (and 650 nm as a control wavelength) on an absorbance plate reader.

Evaluation of Activity of Antibody-Drug Conjugates Against Normal Human Keratinocyte Cell Line The normal control cell line, immortal human keratinocytes, HaCaT cells (China Center for Type Culture Collection (CCTCC), Wuhan University) were cultured in Dulbecco's Modified Eagle Medium (DMEM, Sigma-Aldrich, St. Louis, Mo.) supplemented with 10% FBS, 100 units/mL of penicillin, 100 µg/mL of streptomycin, and 2 mM L-glutamine. Between 2,000 and 10,000 cells were seeded per well of a flat-bottom 96-well tissue culture plate, and subsequently incubated with various concentrations of the test articles (conjugates) in culture media for up to 5 days at 37° C., humidified, 5% $CO_2$ incubator. Positive cell killing control was established by a 2-hour pre-treatment of control wells with 10% ethanol in culture media. Viability of the cells remaining after treatment in each well was determined via the MTS cell viability assay (3-(4,5-dimethylthiazol-2-yl)-5-(3-carboxymethoxyphenyl)-2-(4-sulfophenyl)-2H-tetrazolium, inner salt (MTS), Promega, Madison, Wis.) by addition of 20-40 ul of reagent per well. The MTS assay was then incubated between 30 min and 2 hours, and subsequently analyzed by measuring absorbance of each well at 490 nm (and 650 nm as a control wavelength) on an absorbance plate reader.

Cytotoxic Activity of Unconjugated Anti-Human Cathepsin D Antibody

Figure 7:
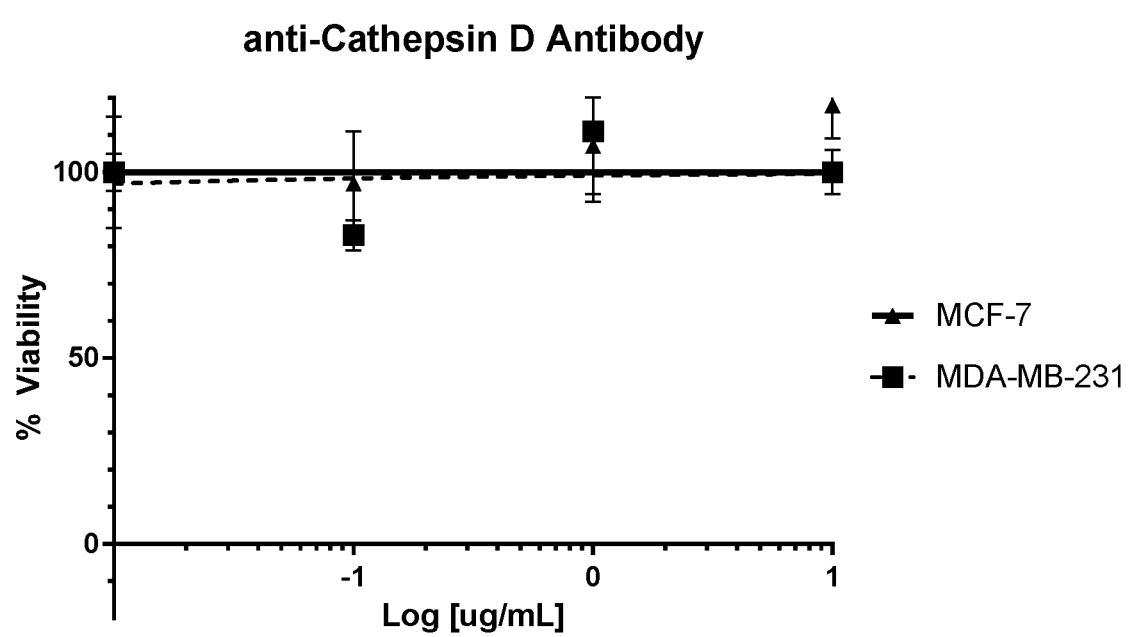
FIG. 7 is a graph depicting the measurement of the cytotoxic activity of the unconjugated ('naked') anti-human cathepsin D antibody against the breast cancer cell lines, MCF-7 and MDA-MB-231, by a colorimetric cell proliferation assay (MTS) conducted the same as the measurement of the activity of antibody-drug conjugates.

MCF-7 and MDA-MB-231 were cultured as described above and treated with unconjugated ('naked') anti-human cathepsin D antibody. The effect of the naked antibody was assessed by MTS assay as described above for the antibody drug conjugates. The results are shown in FIG. 7. The naked antibody had no statistically significant effect on viability.

TABLE 1

| Candidate | Linker/Payload/(Target) | Linker Chemistry | Drug-Antibody Ratio (DAR) |
|---|---|---|---|
| IMB-101 | SMCC-DM1 | Stable | ~8 |
| IMB-102 | SPDB-DM4 | Labile | ~9-10 |
| IMB-991 | SMCC-DM1 Isotype | Stable | ~8 |
| IMB-992 | SPDB-DM4 Isotype | Labile | ~8 |
| IMB-701 | SMCC-DM1 Anti-EGFR | Stable | nd |
| IMB-702 | SPDB-DM4 Anti-EGFR | Labile | nd | nd = not determined

The 50% inhibitory concentrations (IC50) calculated for the antibody-drug conjugates tested on the MCF-7, MDA-MB-231 and HaCaT cell lines is provided in Table 2. (Data corresponds to FIGS. 1-6)

TABLE 2

| Cells | ADC | Target | IC50 (ug/mL) |
|---|---|---|---|
| MCF-7 | IMB-101 | Cathepsin D | 1.3 |
| | IMB-991 | Isotype | >1,000 |
| | IMB-701 | EGFR | 0.9 |
| | IMB-102 | Cathepsin D | 0.15 |
| | IMB-992 | Isotype | >1,000 |
| | IMB-702 | EGFR | 0.23 |
| MDA-MB-231 | IMB-101 | Cathepsin D | 9.6 |
| | IMB-991 | Isotype | >1,000 |

TABLE 2-continued

| Cells | ADC | Target | IC50 (ug/mL) |
|---|---|---|---|
| | IMB-701 | EGFR | 4.1 |
| | IMB-102 | Cathepsin D | 0.6 |
| | IMB-992 | Isotype | >500 |
| | IMB-702 | EGFR | 0.7 |
| HaCaT | IMB-101 | Cathepsin D | 85 |
| | IMB-701 | EGFR | 1.7 |
| | IMB-102 | Cathepsin D | 42 |
| | IMB-702 | EGFR | 0.7 |

Example 2

Evaluation of Activity of Antibody-Drug Conjugates Against Prostate Cancer Cells The conjugates described in Example 1 were used to test their ability to selectively kill prostate cancer cells.

The LNCaP (ATCC, Manassas, Va.) prostate cancer cells were cultured in Roswell Park Memorial Institute (RPMI) 1640 (Sigma-Aldrich, St. Louis, Mo.) supplemented with 10% FBS, 100 units/mL of penicillin, 100 μg/mL of streptomycin, and 2 mM L-glutamine. Between 2,000 and 10,000 cells were seeded per well of a flat-bottom 96-well tissue culture plate, and subsequently incubated with various concentrations of the test articles (conjugates) in culture media for up to 5 days at 37° C., humidified, 5% $CO_2$ incubator. Positive cell killing control was established by a 2-hour pre-treatment of control wells with 10% ethanol in culture media. Viability of the cells remaining after treatment in each well was determined via the MTS cell viability assay (3-(4,5-dimethylthiazol-2-yl)-5-(3-carboxymethoxyphenyl)-2-(4-sulfophenyl)-2H-tetrazolium, inner salt (MTS), Promega, Madison, Wis.) by addition of 20-40 ul of reagent per well. The MTS assay was then incubated between 30 min and 2 hours, and subsequently analyzed by measuring absorbance of each well at 490 nm (and 650 nm as a control wavelength) on an absorbance plate reader.

Figure 8:
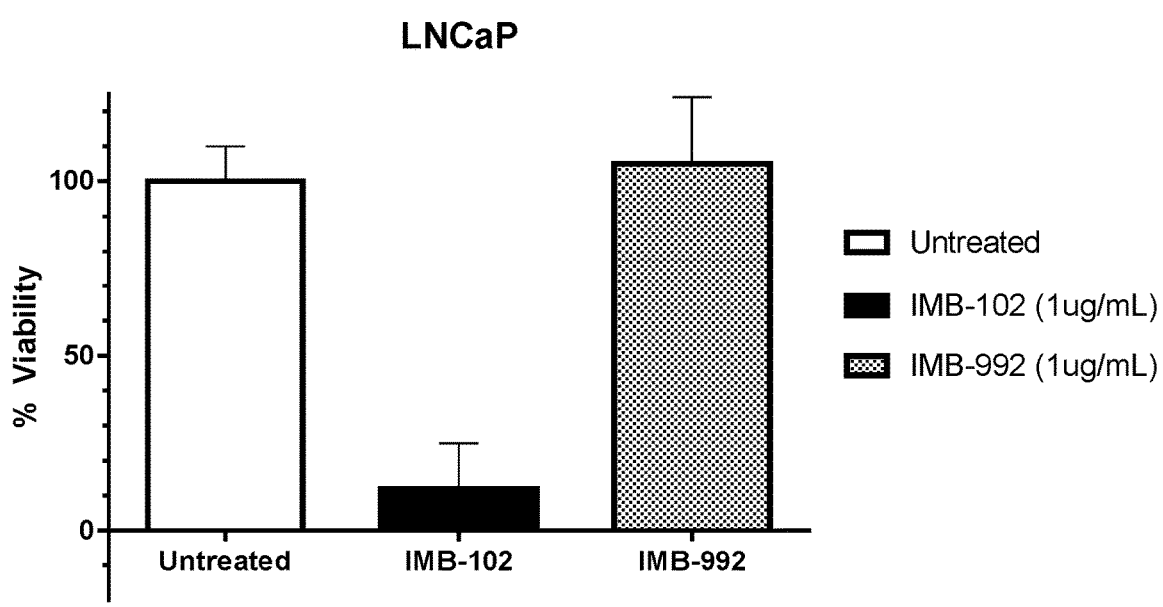
FIG. 8 is a graph depicting the measurement of cytotoxic activity SPDB-DM4 antibody-drug conjugates of anti-human cathepsin D against the prostate cancer cell line, LNCaP, by a colorimetric cell proliferation assay (MTS). IMB-102—anti-human cathepsin D-SPDB-DM4; IMB-992—isotype-matched monoclonal-SPDB-DM4.

As shown in FIG. 8, the cathepsin D conjugate IMB-102 reduced the viability of LNCaP cells in a statistically significant manner. IMB-992 which is the isotype-matched monoclonal control for SPDB-DM4 had no statistically significant toxicity.

Example 3

Evaluation of Activity of Additional Cathepsin D Antibody-Drug Conjugates Against Breast Cancer Cells Conjugates were made from other antibodies binding cathepsin D following the methods described in Example 1 and evaluated for their ability to selectively kill cancer cells as in Example 1.

Conjugates with SMCC-DM1 and SPDB-DM4 were made using the cathepsin D antibody clone 3F12-1B9 (Abnova, Taipei, Taiwan) and cathepsin D antibody M1G8 (available from Dr. Marcel Garcia (Institut des Biomolécules Max Mousseron (IBMM), France). The M1G8 clone recognizes the native forms of cathepsin D and procathepsin D with high sub-nM affinity (Laurent-Matha et al. 1998; Garcia et al. 1985.)

The conjugates of M1G8 and 3F12-1B9 antibodies with SMCC-DM1 and SPDB-DM4 have been demonstrated in cell culture assays evaluating toxicity against breast cancer cell lines, using the methods in Example 1, to selectively target and kill cancer cells over normal cells with comparable efficacy to IMB-101 and IMB-102 antibody-drug conjugates, showing similar cytotoxicity specific for cancer cells.

Example 4

Reinternalization Assay to Determine if a Conjugate or Targeting Agent Bound to a Target Antigen is Recaptured by Cells To measure the ability of a conjugate or targeting agent binding a target antigen such as cathepsin D (such as antibody binding cathepsin D) to be reinternalized by cells, a reinternalization assays can be conducted. This requires the conjugation of the targeting agent to a pH-responsive fluorescent label, such as the pHrodo Red label, which is a pH-sensitive dye whose spectral (fluorescence) properties change in response to lowering of pH. The pHrodo Red succinimidyl (NHS) ester reagent can be used for direct labeling of the targeting agent (Molecular Probes, Life Technologies, Carlsbad, Calif., US) as following:

Resuspend pHrodo Red NHS in DMOS to a stock concentration of 10.2 mM. Use the solution immediately.

Exchange the targeting agent into a 0.1 M sodium bicarbonate buffer, pH 8.3 to a concentration of at least 1 mg/mL.

Determine the amount of reactive dye to use that will give a dye to protein molar ratio (MR) of 5-20 moles of dye per mole of protein. Add the appropriate amount of reactive dye to the protein solution in sodium bicarbonate buffer and mix. Incubate for 15-60 minutes at room temperature (protect from light).

Clean up the labeled targeting agent using gel filtration, dialysis or diafiltration (for example, with a Sephadex G column or Amicon-Ultra 0.5 units) to remove unreacted label.

Use the pHrodo Red: targeting agent conjugate for the reinternalization assay. Either MCF-7 cells or other cell lines can be used for the assay, with or without added recombinant human cathepsin D. The MCF-7 (ATCC, Manassas, Va.) breast cancer cells are cultured in Dulbecco's Modified Eagle Medium (DMEM, Sigma-Aldrich, St. Louis, Mo.) supplemented with 10% FBS, 100 units/mL of penicillin, 100 μg/mL of streptomycin, and 2 mM L-glutamine. Seed between 2,000 and 10,000 cells per well of a flat-bottom 96-well tissue culture plate (ideally, fluorescence assay clear-bottom plates), and subsequently incubate with various concentrations of the labeled test articles (pHrodo Red conjugates) in culture media for 1 to 24 hours at 37° C., humidified, 5% $CO_2$ incubator. Use unlabeled and labeled isotype controls to establish background and baseline. Analyzed cultures by measuring fluorescence of each well at 560 nm on a multimodal plate reader. Positive control can be established in wells containing the pHrodo Red-conjugate but no cells that has been artificially acidified to a pH 4 (and similarly to pH 8 for a negative control). The amount of fluorescence observed is proportional to the extent of internalization of the labeled targeting agent.

REFERENCES

Abbott, D. E., N. V. Margaryan, et al. (2010). "Reevaluating cathepsin D as a biomarker for breast cancer: serum activity levels versus histopathology." *Cancer Biol Ther* 9(1): 23-30.

Barok, M., H. Joensuu, et al. (2014). "Trastuzumab emtansine: mechanisms of action and drug resistance." *Breast Cancer Res* 16(2): 209.

Beaujouin, M., C. Prebois, et al. (2010). "Pro-cathepsin D interacts with the extracellular domain of the beta chain of LRP1 and promotes LRP1-dependent fibroblast outgrowth." *J Cell Sci* 123 (Pt 19): 3336-3346.

Benes, P., V. Vetvicka, et al. (2008). "Cathepsin D—many functions of one aspartic protease." *Crit Rev Oncol Hematol* 68(1): 12-28.

Bouchard, H., C. Viskov, et al. (2014). "Antibody-drug conjugates—a new wave of cancer drugs." *Bioorg Med Chem Lett* 24(23): 5357-5363.

Capony, F., T. Braulke, et al. (1994). "Specific mannose-6-phosphate receptor-independent sorting of pro-cathepsin D in breast cancer cells." *Exp Cell Res* 215(1): 154-163.

Chai, Y., W. Wu, et al. (2012). "The potential prognostic value of cathepsin D protein in serous ovarian cancer." *Arch Gynecol Obstet* 286(2): 465-471.

Chari, R. V. (2008). "Targeted cancer therapy: conferring specificity to cytotoxic drugs." *Acc Chem Res* 41(1): 98-107.

Derocq, D., C. Prebois, et al. (2012). "Cathepsin D is partly endocytosed by the LRP1 receptor and inhibits LRP1-regulated intramembrane proteolysis." *Oncogene* 31(26): 3202-3212.

Dian, D., T. Vrekoussis, et al. (2012). "Expression of cathepsin-D in primary breast cancer and corresponding local recurrence or metastasis: an immunohistochemical study." *Anticancer Res* 32(3): 901-905.

El Melegy, N. T., H. A. Aboulella, et al. (2010). "Potential biomarkers for differentiation of benign prostatic hyperplasia and prostate cancer." *Br J Biomed Sci* 67(3): 109-112.

Fukuda, M. E., Y. Iwadate, et al. (2005). "Cathepsin D is a potential serum marker for poor prognosis in glioma patients." *Cancer Res* 65(12): 5190-5194.

Gandour-Edwards, R., B. Trock, et al. (1999). "Predictive value of cathepsin-D for cervical lymph node metastasis in head and neck squamous cell carcinoma." *Head Neck* 21(8): 718-722.

Hara, I., H. Miyake, et al. (2002). "Serum cathepsin D and its density in men with prostate cancer as new predictors of disease progression." *Oncol Rep* 9(6): 1379-1383.

Herz, J. and D. K. Strickland (2001). "LRP: a multifunctional scavenger and signaling receptor." *J Clin Invest* 108(6): 779-784.

Hinrichs, C. S. and N. P. Restifo (2013). "Reassessing target antigens for adoptive T-cell therapy." *Nat Biotechnol* 31(11): 999-1008.

Huang, L., Z. Liu, et al. (2013). "A prognostic model for triple-negative breast cancer patients based on node status, cathepsin-D and Ki-67 index." *PLoS One* 8(12): e83081.

Khalkhali-Ellis, Z. and M. J. Hendrix (2014). "Two Faces of Cathepsin D: Physiological Guardian Angel and Pathological Demon." *Biol Med (Aligarh)* 6(2).

Kokkonen, N., A. Rivinoja, et al. (2004). "Defective acidification of intracellular organelles results in aberrant secretion of cathepsin D in cancer cells." *J Biol Chem* 279(38): 39982-39988.

Laurent-Matha, V., M. R. Farnoud, et al. (1998). "Endocytosis of pro-cathepsin D into breast cancer cells is mostly independent of mannose-6-phosphate receptors." *J Cell Sci* 111 (Pt 17): 2539-2549.

Laurent-Matha, V., A. Lucas, et al. (2002). "Procathepsin D interacts with prosaposin in cancer cells but its internalization is not mediated by LDL receptor-related protein." *Exp Cell Res* 277(2): 210-219.

Lentari, I., I. Segas, et al. (2002). "The importance of cathepsin's-D tissular detection in laryngeal squamous cell carcinoma." *Acta Otorhinolaryngol Belg* 56(4): 383-389.

Mbeunkui, F., B. J. Metge, et al. (2007). "Identification of differentially secreted biomarkers using LC-MS/MS in isogenic cell lines representing a progression of breast cancer." *J Proteome Res* 6(8): 2993-3002.

Merseburger, A. S., J. Hennenlotter, et al. (2005). "Cathepsin D expression in renal cell cancer-clinical implications." *Eur Urol* 48(3): 519-526.

Miyake, H., I. Hara, et al. (2003). "Prediction of the extent of prostate cancer by the combined use of systematic biopsy and serum level of cathepsin D." *Int J Urol* 10(4): 196-200.

Nomura, T. and N. Katunuma (2005). "Involvement of cathepsins in the invasion, metastasis and proliferation of cancer cells." *J Med Invest* 52(1-2): 1-9.

Park, H. D., E. S. Kang, et al. (2012). "Serum CA19-9, cathepsin D, and matrix metalloproteinase-7 as a diagnostic panel for pancreatic ductal adenocarcinoma." *Proteomics* 12(23-24): 3590-3597.

Perez, E. A. (2008). "Cardiac toxicity of ErbB2-targeted therapies: what do we know?" *Clin Breast Cancer* 8 Suppl 3: S114-120.

Qi, Y. J., D. G. Ward, et al. (2014). "Proteomic profiling of N-linked glycoproteins identifies ConA-binding procathepsin D as a novel serum biomarker for hepatocellular carcinoma." *Proteomics* 14(2-3): 186-195.

Salama, R. H., T. H. Selem, et al. (2013). "Urinary tumor markers could predict survival in bladder carcinoma." *Indian J Clin Biochem* 28(3): 265-271.

Senter, P. D. (2009). "Potent antibody drug conjugates for cancer therapy." *Curr Opin Chem Biol* 13(3): 235-244.

Sloman, A., F. D'Amico, et al. (1996). "Immunohistochemical markers of prolonged survival in small cell carcinoma of the lung. An immunohistochemical study." *Arch Pathol Lab Med* 120(5): 465-472.

Trail, P. (2013). "Antibody Drug Conjugates as Cancer Therapeutics." *Antibodies* 2(1): 113-129.

Tumminello, F. M., G. Leto, et al. (1996). "Cathepsin D, B and L circulating levels as prognostic markers of malignant progression." *Anticancer Res* 16(46): 2315-2319.

Vashishta, A., S. S. Ohri, et al. (2009). "Pleiotropic effects of cathepsin D." *Endocr Metab Immune Disord Drug Targets* 9(4): 385-391.

Vetvicka, V. and M. Fusek (2012). "Procathepsin D as a tumor marker, anti-cancer drug or screening agent." *Anticancer Agents Med Chem* 12(2): 172-175.

Wang, Z. and X. Zhao (1998). "[Expression and prognostic relation of cathepsin D in non-small cell lung cancer tissues and lymph nodes]." *Zhonghua Jie He He Hu Xi Za Zhi* 21(3): 164-166.

Wozniak, B., C. Mila-Kierzenkowska, et al. (2008). "The effect of combined therapy on activity of cathepsin D and alpha-1-antitrypsin in the blood serum of women with cervical cancer." *Eur J Gynaecol Oncol* 29(6): 617-619.

M. Chambon, X. Rebillard, H. Rochefort, J. P. Brouillet, P. Baldet and J. Guiter, T. Maudelonde. Cathepsin D cytosolic assay and immunohistochemical quantification in human prostate tumors, Prostate 24 (1994), 320-325.

R. Makar, A. Mason, J. M. Kittelson and G. T. Bowden, A. E. Cress, R. B. Nagle. Immunohistochemical analysis of cathepsin D in prostate carcinoma, Mod Pathol 7 1994), 747-751.

J. S. Ross, T. Nazeer, H. L. Figge, H. A. Fisher and M. D. Rifkin, Quantitative immunohistochemical determination of cathepsin D levels in prostatic carcinoma biopsies. Correlation with tumor grade, stage, PSA level, and DNA ploidy status, Am J Clin Pathol 104 (1995), 36-41.

Nicotra G1, Castino R, Follo C, Peracchio C, Valente G, Isidoro C. The dilemma: does tissue expression of cathepsin D reflect tumor malignancy? The question: does the assay truly mirror cathepsin D mis-function in the tumor? Cancer Biomark. 2010; 7(1):47-64. doi: 10.3233/CBM-2010-0143.

Garcia et al. Characterization of Monoclonal Antibodies to the Estrogen-regulated Mr 52,000 Glycoprotein and Their Use in MCF7 Cells. 1985. Cancer Res Capony et al. Increased Secretion, Altered Processing, and Glycosylation of Pro-Cathepsin D in Human Mammary Cells. 1989. Cancer Res

The invention claimed is:

1. A conjugate comprising:
   I. a. an antibody that specifically binds human cathepsin D;
      b. a cytotoxic moiety linked indirectly to the antibody, the cytotoxic moiety selected from the group consisting of an auristatin, a dolastatin, a maytansinoid, a tubulysin, a cryptophycins, and a calicheamicin;
      c. and a labile linker linking the antibody and cytotoxic moiety, the labile linker derived from a cross-linking reagent selected from the group consisting of N-succinimydyl-3-(2-pyridyldithio)propionate (SPDP), N-succinimidyl 4-(2-(SPDB), and N-succinimidyl-4-(2-pyridyldithio)2-sulfo-butanoate (sulfo-SPDB);
   wherein the antibody is selected from anti-cathepsin D antibody clone 185111, anti-cathepsin D antibody clone 3F12-1B9 and anti-cathepsin D antibody clone M1G8 or a binding fragment of any of the foregoing; and
   wherein the conjugate is able to bind extracellular cathepsin D and selectively target cancer cells.

2. The conjugate of claim 1, wherein the maytansinoid is selected from N(2')-deacetyl-N(2')-(3-mercapto-1-oxopropyl)-maytansine (DM1), and N(2')-deacetyl-N(2')-(4-mercapto-4-methyl-1-oxopentyl)-maytansine (DM4).

3. The conjugate of claim 1, wherein the linker and cytotoxic moiety comprises N-succinimidyl 4-(maleimidomethyl)cyclohexanecarboxylate (SMCC) linker and N(2')-deacetyl-N(2')-(3-mercapto-1-oxopropyl)-maytansine (DM1) cytotoxic moiety, (SMCC-DM1); or N-succinimidyl 4-(2-pyridyldithio)butanoate (SPDB) linker and N(2')-deacetyl-N(2')-(4-mercapto-4-methyl-1-oxopentyl)-maytansine (DM4) cytotoxic moiety, (SPDB-DM4).

4. The conjugate of claim 3, wherein the linker and cytotoxic moiety comprises N-succinimidyl 4-(2-pyridyldithio)2-sulfo-butanoate linker and N(2')-deacetyl-N(2')-(4-mercapto-4-methyl-1-oxopentyl)-maytansine (DM4) cytotoxic moiety, (Sulfo-SPDB-DM4).

5. The conjugate of claim 4, wherein the cytotoxic moiety and linker to antibody ratio is between 1 and 20.

6. The conjugate of claim 1, wherein the cytotoxic moiety and linker to antibody ratio is between 1 and 20.

7. The conjugate of claim 1, wherein the binding fragment is an Fab fragment or an F(ab')2 fragment.

8. A composition comprising an effective amount of the conjugate of claim 1, a pharmaceutically acceptable salt or solvate thereof, and a pharmaceutically acceptable carrier, diluent or excipient.

9. A method of treating cancer comprising administering to a subject in need thereof an effective amount of the conjugate of claim 1, or a composition comprising said conjugate, wherein the cancer is a solid tumor secreting cathepsin D.

10. The method of claim 9, wherein the subject has one or more metastases.

11. The method of claim 9, wherein a sample of the cancer is assessed for cathepsin D expression prior to administration of the conjugate or the composition.

12. The method of claim 9, wherein the cancer is selected from the group consisting of breast cancer, such as triple-negative breast cancer, prostate cancer, ovarian cancer, endometrial cancer, non-small cell lung cancer (NSCLC), hepatocellular carcinoma (HCC), head & neck squamous cell carcinoma (HNSCC), bladder cancer, pancreatic cancer, glioblastoma multiforme (GBM), small-cell lung cancer, melanoma, and renal cell carcinoma.

* * * * *

UNITED STATES PATENT AND TRADEMARK OFFICE
CERTIFICATE OF CORRECTION

PATENT NO. : 10,780,179 B2
APPLICATION NO. : 15/558906
DATED : September 22, 2020
INVENTOR(S) : Anton Neschadim Page 1 of 1

It is certified that error appears in the above-identified patent and that said Letters Patent is hereby corrected as shown below:

In the Claims

Column 35, Line 17 Claim 1 should read as follows:
1. A conjugate comprising:
    I.    a. an antibody that specifically binds human cathepsin D;
        b. a cytotoxic moiety linked indirectly to the antibody, the cytotoxic moiety selected from the group consisting of an auristatin, a dolastatin, a maytansinoid, a tubulysin, a cryptophycins, and a calicheamicin;
        c. and a labile linker linking the antibody and cytotoxic moiety, the labile linker derived from a cross-linking reagent selected from the group consisting of N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), and N-succinimidyl-4-(2-pyridyldithio)2-sulfo-butanoate (sulfo-SPDB);
wherein the antibody is selected from anti-cathepsin D antibody clone 185111, anti-cathepsin D antibody clone 3F12-1B9 and anti-cathepsin D antibody clone M1G8 or a binding fragment of any of the foregoing; and
wherein the conjugate is able to bind extracellular cathepsin D and selectively target cancer cells.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*